US006989146B2

(12) United States Patent  
Albani et al.

(10) Patent No.: US 6,989,146 B2  
(45) Date of Patent: Jan. 24, 2006

(54) STRESS PROTEINS AND PEPTIDES AND METHODS OF USE THEREOF

(75) Inventors: Salvatore Albani, Encinitas, CA (US); Berent J. Prakken, Pieter Saenredamstraat (NL)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/828,574

(22) Filed: Apr. 6, 2001

(65) Prior Publication Data

US 2002/0146759 A1  Oct. 10, 2002

Related U.S. Application Data

(60) Provisional application No. 60/224,104, filed on Aug. 9, 2000.

(51) Int. Cl.  
A61K 39/00    (2006.01)  
A61K 39/02    (2006.01)  
A61K 39/04    (2006.01)  
C07K 14/00    (2006.01)

(52) U.S. Cl. .............................. 424/185.1; 424/190.1; 424/234.1; 424/248.1; 530/300

(58) Field of Classification Search .............. 424/185.1, 424/190.1, 234.1, 248.1, 184.1; 530/300, 530/350  
See application file for complete search history.

(56) References Cited

U.S. PATENT DOCUMENTS

| | | | |
|---|---|---|---|
| 4,654,419 A | 3/1987 | Vaughan et al. | |
| 4,683,295 A | 7/1987 | Carson | |
| 4,732,757 A | 3/1988 | Stolle et al. | |
| 5,116,725 A | 5/1992 | Vaughan et al. | |
| 5,310,732 A | 5/1994 | Carson et al. | |
| 5,541,164 A | 7/1996 | Carson et al. | |
| 5,728,385 A | 3/1998 | Classen | |
| 5,773,570 A | 6/1998 | Carson et al. | |
| 5,891,435 A | 4/1999 | Muir et al. | |
| 5,922,567 A | 7/1999 | Au-Young et al. | |
| 5,928,644 A | * 7/1999 | Russell-Jones et al. | |
| 5,993,803 A | 11/1999 | Cohen et al. | |
| 6,007,821 A | 12/1999 | Srivastava et al. | |
| 6,037,135 A | 3/2000 | Kubo et al. | |
| 6,455,503 B1 | * 9/2002 | Srivastava | |

FOREIGN PATENT DOCUMENTS

| | | |
|---|---|---|
| EP | 0262710 A1 * | 4/1988 |
| WO | WO90/14835 | 12/1990 |
| WO | 95/25744 * | 9/1995 |
| WO | WO95/31984 | 11/1995 |
| WO | 96/10039 * | 4/1996 |
| WO | WO 97/11966 | 4/1997 |
| WO | WO 97/34002 | 9/1997 |
| WO | WO 99/61916 | 12/1999 |

OTHER PUBLICATIONS

Guichard et al (PNAS USA vol. 91, pp. 9765–9769), Oct. 1994.*

H.C. Meeker, et al. "Analysis of Human Antibodies Epitopes on the 65–Kilodalton Protein of Mycobacterium lepare by Using Synthetic Peptides", *Infection and Immunty, American Society for Microbiology, Washington, D.C, US*, vol. 57, No. 12, 3689–3694, Dec. 1989.

B.J. Prakken et al. "Epitope: Mapping of Hsp60 T Cell Responses in Children with Arthritis by Prediction of Pan–Hla DR. Binding Sites", *Arthritis and Rheumatism, Lippincott, Philadelphia, US*, vol. 42, No. 9 Supplement, S229, Sep. 1999.

B.J. Prakken, et al., "Peptide–induced nasal tolerances for mycobacterial heat shock protein 60 T cell epitope in rats suppresses both adjuvant arthritis and nonmicrobially induced experimental arthritis", *Proceedings of the National Academy of Sciences, USA*, vol. 94, 3284–3289, Apr. 1987.

B.J. Prakken et al., "Identification of Pan–DR Binding T Cell Epitopes of Human and Mycobacterial hsp60 in Patients with Juvenile Idiopathic Arthritis", *Conference of Immunologist*, p. 1, Jan. 1, 2001.

Albani, S., et al., "Positive Selection in Autoimmunity: Abnormal Immune Responses to a Bacterial dnaJ Antigen Determinant in Patients with Early Rheumatoid Arthritis," *Nature Medicine*, vol. 1, No. 5, pp. 448–452, 1995.

Bonnin, D., et al., "MHC–Derived Peptides Drive Positive T Cell Selection in the Thymus: from a Physiological System to an HLA DRBI *0401 Transgenic Mouse Model for Rheumatoid Arthritis?", *Arthritis and Rheumatism*, vol. 39, No. 9 Suppl., p. S160, Oct. 1996.

Auger, I., et al., "HLA–DR4 and HLA–DR10 Motifs that Carry Susceptibility to Rheumatoid Arthritis Bind 70–kD Heat Shock Proteins," *Nature Medicine*, vol. 2, No. 3, pp. 306–310, Mar. 1996.

Albani, et al., "Genetics and Environmental Factors in the Immune Pathogenesis of Rheumatoid Arthritis," *Rheumatic Disease Clinics of North America*, 18/4:729–740, 1992.

Stastney, P., et al., "Immunogenetics of Rheumatoid Arthritis and Juvenile Arthritis", *Recenti Progressi in Medicina*, vol. 82, No. 7–8, pp. 409–416, 1991.

(Continued)

*Primary Examiner*—Mark Navarro  
(74) *Attorney, Agent, or Firm*—DLA Piper Rudnick Gray Cary US LLP

(57) ABSTRACT

Provided are HLA pan DR peptides and methods of using such peptides to modulate, block, or inhibit immune responses in treatment of immune-mediated diseases and conditions, such as inflammatory and autoimmune diseases, cancer, and microbial infections. The peptides and methods are useful diagnostically to screen peptide or peptide analogs that can inhibit the pathogenic immune response or upregulate an immune response against aberrant or invading cells, to monitor efficacy or therapeutic use and to identify other agents that may be effective to inhibit or modulate the immune response.

43 Claims, 13 Drawing Sheets

OTHER PUBLICATIONS

Nepom, G., "Prediction of Susceptibility to Rheumatoid Arthritis by Human Leukocyte Antigen Genotyping" *Rheumatic Disease Clinics of North America*, vol. 18, No. 4, pp. 785–792, Nov., 1992.

Weyand, C., et al., "The Influence of HLA–DRBI Genes on Disease Severity in Rheumatoid Arthritis," Annals of Internal Medicine, vol. 117, No. 10, pp. 801–806, Nov. 15, 1992.

Fairchild, P., et al., "Peptide–MHC Interaction in Autoimmunity," *Current Opinion in Immunology*, vol. 4, pp. 748–753, 1992.

Life, P.F., et al., "Synovial Fluid Antigen–Presenting Cells Unmask Peripheral Blood T Cell Responses to Bacterial Antigens in Inflammatory Arthritis," *Clin. Exp. Immunol.* vol. 79, pp. 189–194, 1990.

Van Den Broek, M.F., et al., "Protection Against Streptococcal Cell Wall–Induced Arthritis by Pretreatment with the 65–kD Mycobacterial Heat Shock Protein," *J. Exp. Med.*, vol. 170, pp. 449–466, Aug., 1989.

Anderton, S.M., et al. "Activation of T Cells Recognizing Self 60–kD Heat Shock Protein Can Protect Against Experimental Arthritis,"*J. Exp. Med.*, vol. 181, pp. 943–952, Mar. 1995.

Albani, S., et al., "A Multistep Molecular Mimiery Hypothesis for the Pathogenesis of Rheumatoid Arthritis," *Immunology Today*, vol. 17, No. 10, pp. 466–470, Oct., 1996.

Anderton et al., "Differential Mycobacterial 65–kDa Heat Shock Protein T Cell Epitope Recognition after Adjuvant Arthritis–Inducing or Protective Immunization Protocols," *J. Immunology* 152:3656–64, 1994.

Albani et al, "HLA Binding Studies Support a Role for the QKRAA Susceptibility Sequence to Rheumatoid Arthritis (RA) in Positive Selection and Activation of Pathogenic T Lymphocytes," *Arthritis and Rheumatism*, 38/9 Suppl., p. S181, Abstract #173, 1995.

Plotkin, S.A., et al., "New Technologies for Making Vaccines," *Vaccines*, pp. 568–575, 1988.

Albani, S., et al., "Molecular Basis for the Association Between HLA DR4 and Rheumatoid Arthritis. From the Shared Epitope Hypothesis to a Peptidic Model of Rheumatoid Arthritis," *Clin. Biochem.* vol. 25, pp. 209–212, 1992.

La Cava, A., et al., "The QKRAA Disease Susceptibility Sequence for Rheumatoid Arthritis (RA) is a B Cell Epitope Shared by the Epstein–Barr Virus (EBV) Protein gp110 and the E. Coli Heat Shock Protein dnaJ Possible Implications for Disease Pathogenesis," *Arthritis & Rheum.* 36(9) Suppl. pp. S127 Abstract 1993.

Asseldonk, M., et al., "Cloning, Nucleotide Sequence, and Regulatory Analysis of the *Lactococcus Lactis dnaJ* Gene,", *Journal of Bacteriology*, 175(6), pp. 1637–1644, Mar. 1993.

Bardwell, J.C.A., et al., "The Nucleotide Sequence of the *Escherichia coli K12 dnaJ*+Gene," *The Journal of Biological Chemistry*, vol. 261, No. 4, pp. 1782–1785, Feb. 5, 1986.

Ohki, M., et al., "Nucleotide Sequence of the *Escherichia coli dnaJ* Gene and Purification of the Gene Product*", The Journal of Biological Chemistry, vol. 261, No. 4, pp. 1778–1781, 1986.

Albani, S., et al., "The Susceptibility Sequence to Rheumatoid Arthritis is a Cross–Reactive B Cell Epitope Shared by the *Escherichia Coli* Heat Shock Protein dnaJ and the Histocompatibility Leukocyte Antigen DRB10401 Molecule," *J. Clin. Invest.*, vol. 89, pp. 327–331, 1992.

van Eden, W., et al., "Cloning of the Mycobacterial Epitope Recognized by T Lymphocytes in Adjuvant Arthritis," *Nature*, vol. 331, pp. 171–173, Jan. 14, 1988.

Silver, P.A., et al. "Eukaryotic DnaJ Homologs and the Specificity of Hsp70 Activity," *Cell*, vol. 74, pp. 5–6, Jul. 16, 1993.

Zuber et al., "Cloning, Sequencing and Expression of *dnaJ* gene of *Coxiella Burnetii,*" *Gene*, vol. 152 pp. 99–102, 1995.

DeGraeff–Meeder, E.R., et al., "Recognition of Human 60kD Heat Shock Protein by Mononuclear Cells from Patients with Juvenile Chronic Arthritis," *The Lancet*, vol. 337, pp. 1368–1372, Jun. 8, 1991.

Brackertz et al, "OM–8980 in Rheumatoid Arthritis: A 6–Month Double Blind Placebo Controlled Multicenter Study," *Journal of Rheumatology*, vol. 16, pp. 19–23, 1989.

Marsh, S.G.E., et al, "HLA Class II Nucleotide Sequences, 1991," *Tissue Antigens*, vol. 37, pp. 181–189, 1991.

Albani, S., et al., "Immune Responses to the Escherichia Coli dnaJ Heat Shock Protein in Juvenile Rheumatoid Arthritis and their Correlation with Disease Activity," *The Journal of Pediatrics*, vol. 124, No. 4, pp. 561–565, Apr. 1994.

Schoel et al., "Elongated Peptides, Not the Predicted Nonapeptide Stimulate A Major Histocompatibility Complex Class I–restricted Cytotoxic T Lymphocyte Clone with Specificity for a Bacterial Heat Shock Protein," *European Journal of Immunology*, vol. 24, No. 12, 1994, pp. 3161–3169.

* cited by examiner

SEQUENCE LISTING

<160> NUMBER OF SEQ ID NOS: 23

<210> SEQ ID NO 1
<211> LENGTH: 573
<212> TYPE: PRT
<213> ORGANISM: Homo sapiens

<400> SEQUENCE: 1

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

-continued

```
Gly Ala Asp Ala Arg Ala Leu Met Leu Gln Gly Val Asp Leu Leu Ala
             35                  40                  45
Asp Ala Val Ala Val Thr Met Gly Pro Lys Gly Arg Thr Val Ile Ile
 50                  55                  60
Glu Gln Ser Trp Gly Ser Pro Lys Val Thr Lys Asp Gly Val Thr Val
 65                  70                  75                  80
Ala Lys Ser Ile Asp Leu Lys Asp Lys Tyr Lys Asn Ile Gly Ala Lys
                 85                  90                  95
Leu Val Gln Asp Val Ala Asn Asn Thr Asn Glu Glu Ala Gly Asp Gly
             100                 105                 110
Thr Thr Thr Ala Thr Val Leu Ala Arg Ser Ile Ala Lys Glu Gly Phe
         115                 120                 125
Glu Lys Ile Ser Lys Gly Ala Asn Pro Val Glu Ile Arg Arg Gly Val
     130                 135                 140
Met Leu Ala Val Asp Ala Val Ile Ala Glu Leu Lys Lys Gln Ser Lys
145                 150                 155                 160
Pro Val Thr Thr Pro Glu Glu Ile Ala Gln Val Ala Thr Ile Ser Ala
                 165                 170                 175
Asn Gly Asp Lys Glu Ile Gly Asn Ile Ile Ser Asp Ala Met Lys Lys
             180                 185                 190
Val Gly Arg Lys Gly Val Ile Thr Val Lys Asp Gly Lys Thr Leu Asn
         195                 200                 205
Asp Glu Leu Glu Ile Ile Glu Gly Met Lys Phe Asp Arg Gly Tyr Ile
     210                 215                 220
Ser Pro Tyr Phe Ile Asn Thr Ser Lys Gly Gln Lys Cys Glu Phe Gln
225                 230                 235                 240
Asp Ala Tyr Val Leu Leu Ser Glu Lys Lys Ile Ser Ser Ile Gln Ser
                 245                 250                 255
Ile Val Pro Ala Leu Glu Ile Ala Asn Ala His Arg Lys Pro Leu Val
             260                 265                 270
Ile Ile Ala Glu Asp Val Asp Gly Glu Ala Leu Ser Thr Leu Val Leu
         275                 280                 285
Asn Arg Leu Lys Val Gly Leu Gln Val Val Ala Val Lys Ala Pro Gly
     290                 295                 300
Phe Gly Asp Asn Arg Lys Asn Gln Leu Lys Asp Met Ala Ile Ala Thr
305                 310                 315                 320
Gly Gly Ala Val Phe Gly Glu Glu Gly Leu Thr Leu Asn Leu Glu Asp
                 325                 330                 335
Val Gln Pro His Asp Leu Gly Lys Val Gly Glu Val Ile Val Thr Lys
             340                 345                 350
Asp Asp Ala Met Leu Leu Lys Gly Lys Gly Asp Lys Ala Gln Ile Glu
         355                 360                 365
Lys Arg Ile Gln Glu Ile Ile Glu Gln Leu Asp Val Thr Thr Ser Glu
     370                 375                 380
Tyr Glu Lys Glu Lys Leu Asn Glu Arg Leu Ala Lys Leu Ser Asp Gly
385                 390                 395                 400
Val Ala Val Leu Lys Val Gly Gly Thr Ser Asp Val Glu Val Asn Glu
                 405                 410                 415
Lys Lys Asp Arg Val Thr Asp Ala Leu Asn Ala Thr Arg Ala Ala Val
             420                 425                 430
Glu Glu Gly Ile Val Leu Gly Gly Gly Cys Ala Leu Leu Arg Cys Ile
         435                 440                 445
```

-continued

```
Pro Ala Leu Asp Ser Leu Thr Pro Ala Asn Glu Asp Gln Lys Ile Gly
    450                 455                 460
Ile Glu Ile Ile Lys Arg Thr Leu Lys Ile Pro Ala Met Thr Ile Ala
465                 470                 475                 480
Lys Asn Ala Gly Val Glu Gly Ser Leu Ile Val Glu Lys Ile Met Gln
                485                 490                 495
Ser Ser Ser Glu Val Gly Tyr Asp Ala Met Ala Gly Asp Phe Val Asn
                500                 505                 510
Met Val Glu Lys Gly Ile Ile Asp Pro Thr Lys Val Val Arg Thr Ala
            515                 520                 525
Leu Leu Asp Ala Ala Gly Val Ala Ser Leu Leu Thr Thr Ala Glu Val
        530                 535                 540
Val Val Thr Glu Ile Pro Lys Glu Glu Lys Asp Pro Gly Met Gly Ala
545                 550                 555                 560
Met Gly Gly Met Gly Gly Gly Met Gly Gly Gly Met Phe
                565                 570
```

```
<210> SEQ ID NO 2
<211> LENGTH: 15
<212> TYPE: PRT
<213> ORGANISM: Mycobacterium

<400> SEQUENCE: 2

Gly Glu Ala Leu Ser Thr Leu Val Val Asn Lys Ile Arg Gly Thr
1               5                   10                  15

<210> SEQ ID NO 3
<211> LENGTH: 15
<212> TYPE: PRT
<213> ORGANISM: Homo sapiens

<400> SEQUENCE: 3

Gly Glu Ala Leu Ser Thr Leu Val Leu Asn Arg Leu Lys Val Gly
1               5                   10                  15

<210> SEQ ID NO 4
<211> LENGTH: 15
<212> TYPE: PRT
<213> ORGANISM: Mycobacterium

<400> SEQUENCE: 4

Pro Tyr Ile Leu Leu Val Ser Ser Lys Val Ser Thr Val Lys Asp
1               5                   10                  15

<210> SEQ ID NO 5
<211> LENGTH: 15
<212> TYPE: PRT
<213> ORGANISM: Homo sapiens

<400> SEQUENCE: 5

Ala Tyr Val Leu Leu Ser Glu Lys Lys Ile Ser Ser Ile Gln Ser
1               5                   10                  15

<210> SEQ ID NO 6
<211> LENGTH: 15
<212> TYPE: PRT
<213> ORGANISM: Mycobacterium

<400> SEQUENCE: 6

Glu Ala Val Leu Glu Asp Pro Tyr Ile Leu Leu Val Ser Ser Lys
1               5                   10                  15
```

```
<210> SEQ ID NO 7
<211> LENGTH: 15
<212> TYPE: PRT
<213> ORGANISM: Homo sapiens

<400> SEQUENCE: 7

Lys Cys Glu Phe Gln Asp Ala Tyr Val Leu Leu Ser Glu Lys Lys
1               5                   10                  15

<210> SEQ ID NO 8
<211> LENGTH: 15
<212> TYPE: PRT
<213> ORGANISM: Mycobacterium

<400> SEQUENCE: 8

Ile Ala Gly Leu Phe Leu Thr Thr Glu Ala Val Val Ala Asp Lys
1               5                   10                  15

<210> SEQ ID NO 9
<211> LENGTH: 15
<212> TYPE: PRT
<213> ORGANISM: Homo sapiens

<400> SEQUENCE: 9

Val Ala Ser Leu Leu Thr Thr Ala Glu Val Val Val Thr Glu Ile
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: dnaJP1 peptide

<400> SEQUENCE: 10

Gln Lys Arg Ala Ala Tyr Asp Gln Tyr Gly His Ala Ala Phe Glu
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Irrelevant dnaJpV peptide

<400> SEQUENCE: 11

Asp Glu Arg Ala Ala Tyr Asp Gln Tyr Gly His Ala Ala Phe Glu
1               5                   10                  15

<210> SEQ ID NO 12
<211> LENGTH: 11
<212> TYPE: PRT
<213> ORGANISM: Artificial sequence
<220> FEATURE:
<223> OTHER INFORMATION: pan-DR binder peptide
<220> FEATURE:
<221> NAME/KEY: MISC_FEATURE
<222> LOCATION: (2)..(2)
<223> OTHER INFORMATION: Xaa is any amino acid

<400> SEQUENCE: 12

Lys Xaa Val Ala Ala Trp Thr Leu Lys Ala Ala
1               5                   10

<210> SEQ ID NO 13
<211> LENGTH: 573
```

```
<212> TYPE: PRT
<213> ORGANISM: Homo sapiens

<400> SEQUENCE: 13

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
            20                  25                  30

Gly Ala Asp Ala Arg Ala Leu Met Leu Gln Gly Val Asp Leu Leu Ala
            35                  40                  45

Asp Ala Val Ala Val Thr Met Glu Pro Lys Gly Arg Thr Val Ile Ile
50                      55                  60

Glu Gln Ser Trp Gly Ser Pro Asn Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95

Leu Val Gln Asp Val Ala Asn Asn Thr Asn Glu Glu Ser Gly Asp Gly
            100                 105                 110

Thr Thr Thr Ala Thr Val Leu Ala Gly Ser Ile Ala Lys Glu Gly Phe
        115                 120                 125

Gln Lys Ile Ser Lys Gly Ala Asn Pro Val Glu Ile Arg Arg Gly Val
    130                 135                 140

Met Leu Ala Val Asp Ala Val Ile Ala Glu Leu Lys Lys Gln Ser Lys
145                 150                 155                 160

Pro Val Thr Thr Pro Glu Glu Ile Ala Gln Val Ala Met Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Val Gln Ser
                245                 250                 255

Ile Val Pro Ala Leu Glu Ile Ala Asn Ala His His Lys Pro Leu Val
            260                 265                 270

Ile Ile Ala Glu Asp Val Asp Gly Glu Ala Leu Ser Thr Leu Ile Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Leu Glu
        355                 360                 365

Lys Arg Ile Gln Glu Ile Ile Gly Gln Leu Asp Val Thr Thr Ser Glu
    370                 375                 380

Tyr Glu Lys Glu Lys Leu Asn Glu Trp Leu Ala Lys Leu Ser Asp Gly
385                 390                 395                 400
```

-continued

```
Val Val Val Leu Lys Phe Gly Gly Thr Ser Asp Val Glu Val Asn Glu
            405                 410                 415
Lys Lys Asp Arg Val Thr Asp Ala Leu Asn Ala Thr Arg Ala Ala Val
            420                 425                 430
Glu Gly Gly Ile Val Leu Gly Gly Phe Ala Leu Leu Arg Cys Ile
            435                 440                 445
Pro Ala Leu Asp Ser Leu Thr Pro Ala Asn Glu Asp Gln Lys Ile Gly
            450                 455                 460
Met Glu Ile Val Lys Arg Thr Leu Lys Ile Pro Ala Met Thr Thr Ala
465                 470                 475                 480
Thr Asn Ala Gly Val Glu Gly Ser Leu Ile Val Glu Lys Ile Met Gln
            485                 490                 495
Asn Ser Ser Glu Val Gly Tyr Asp Ala Met Val Gly Asp Phe Met Asn
            500                 505                 510
Met Val Glu Lys Gly Ile Ile Asp Pro Thr Lys Leu Val Arg Thr Ala
            515                 520                 525
Leu Leu Asp Ala Ala Gly Val Ala Ser Leu Leu Thr Thr Ala Glu Val
            530                 535                 540
Val Val Thr Glu Ile Pro Lys Glu Glu Lys Asp Pro Gly Met Gly Ala
545                 550                 555                 560
Met Gly Gly Met Gly Gly Met Gly Gly Gly Met Phe
            565                 570
```

<210> SEQ ID NO 14
<211> LENGTH: 9
<212> TYPE: PRT
<213> ORGANISM: Mycobacterium

<400> SEQUENCE: 14

Leu Ser Thr Leu Val Val Asn Lys Ile
1               5

<210> SEQ ID NO 15
<211> LENGTH: 9
<212> TYPE: PRT
<213> ORGANISM: Homo sapiens

<400> SEQUENCE: 15

Leu Ser Thr Leu Val Leu Asn Arg Leu
1               5

<210> SEQ ID NO 16
<211> LENGTH: 9
<212> TYPE: PRT
<213> ORGANISM: Mycobacterium

<400> SEQUENCE: 16

Leu Val Ser Ser Lys Val Ser Thr Val
1               5

<210> SEQ ID NO 17
<211> LENGTH: 9
<212> TYPE: PRT
<213> ORGANISM: Mycobacterium

<400> SEQUENCE: 17

Tyr Ile Leu Leu Val Ser Ser Lys Val
1               5

```
<210> SEQ ID NO 18
<211> LENGTH: 9
<212> TYPE: PRT
<213> ORGANISM: Homo sapiens

<400> SEQUENCE: 18

Leu Ser Glu Lys Lys Ile Ser Ser Ile
1               5

<210> SEQ ID NO 19
<211> LENGTH: 9
<212> TYPE: PRT
<213> ORGANISM: Mycobacterium

<400> SEQUENCE: 19

Leu Glu Asp Pro Tyr Ile Leu Leu Val
1               5

<210> SEQ ID NO 20
<211> LENGTH: 9
<212> TYPE: PRT
<213> ORGANISM: Homo sapiens

<400> SEQUENCE: 20

Phe Gln Asp Ala Tyr Val Leu Leu Ser
1               5

<210> SEQ ID NO 21
<211> LENGTH: 9
<212> TYPE: PRT
<213> ORGANISM: Mycobacterium

<400> SEQUENCE: 21

Leu Thr Thr Glu Ala Val Val Ala Asp
1               5

<210> SEQ ID NO 22
<211> LENGTH: 9
<212> TYPE: PRT
<213> ORGANISM: Mycobacterium

<400> SEQUENCE: 22

Phe Leu Thr Thr Glu Ala Val Val Ala
1               5

<210> SEQ ID NO 23
<211> LENGTH: 9
<212> TYPE: PRT
<213> ORGANISM: Homo sapiens

<400> SEQUENCE: 23

Leu Thr Thr Ala Glu Val Val Val Thr
1               5
```

STRESS PROTEINS AND PEPTIDES AND METHODS OF USE THEREOF

CROSS REFERENCE TO RELATED APPLICATIONS

This application claims priority under 35 U.S.C. §119(e)(1) from Provisional Application Ser. No. 60/224,104, filed Aug. 9, 2000, the contents of which is incorporated by reference in its entirety herein.

This application was supported by NIH Grant No. NO1 AR40770-09. Accordingly the U.S. Government may have an interest in this application.

FIELD OF THE INVENTION

This invention relates to novel stress-related peptides and methods of use thereof. In particular, there is provided novel heat shock protein (hsp) peptide sequences useful in modulating inflammatory responses in immune-mediated diseases, ranging from autoimmunity to cancer to infectious diseases.

BACKGROUND

Vertebrates possess the ability to mount an immune response as a defense against pathogens from the environment as well as against aberrant cells, such as tumor cells, which develop internally. This can take the form of innate immunity, which is mediated by NK cells, neutrophils and cells of the monocyte/macrophage lineage, or the form of acquired or active immunity against specific antigens mediated by lymphocytes. Active immune responses can be further subdivided into two arms, the humoral response which entails the production of specific antibodies that serve to neutralize antigens exposed to the systemic circulation and aid in their uptake by professional phagocytic cells, and the cellular arm which is required for recognition of infected or aberrant cells within the body. Often these immunogenic response result in diseases and disorders that cause harm to the organism itself. Such disorder are associated with the recognition of self proteins and cells as foreign and thus trigger an attack upon such cells or cellular proteins. Common autoimmune disorders include, for example, psoriasis, arthritis, lupus, diabetes and others known in the art.

One of most likely scenarios regarding the pathogenesis of an autoimmune disease like type I diabetes, may begin with abnormal regulation of autoreactive T cells either due to bystander activation or due to molecular mimicry. For example, a viral infection or exposure to a superantigen may provide sufficient co-stimulation resulting in activation of few low affinity autoreactive T cells that escape the thymus selection. Abnormal down-regulation of such autoreactive responses may lead to expansion of pathogenic T cells that infiltrate the organ where the recognized antigen is present. A few host-related factors facilitate the transition between non-pathogenic autoreactivity and autoimmune disease: leaky central negative selection allowing the escape of higher numbers of autoreactive precursors; impaired peripheral tolerance due to abnormalities involving receptors or ligands that mediated down-regulation of lymphocyte activity; a bias to generate TH1 pro-inflammatory responses as opposed to more balanced TH1/TH2 responses; high frequency and abnormal activity of professional APCs. Local inflammation and direct destruction of host cells trigger antigen release, uptake by professional APCs and presentation to specific T cells, thus perpetuating a positive feedback that exacerbates the autoimmunity. Simultaneously, normally cryptic, organ-associated antigens may become exposed in the context of activation of professional antigen presenting cells and antigen release, resulting in activation of T cells specific for these other self antigens. Particularly in conditions favoring overall TH1 /TH2 imbalance, the employment of additional specificities may accelerate the disease. It is widely believed that whereas TH1 cytokines like IFN-γ contribute to the pathogenesis of autoimmunity, TH2 cytokines like IL-4 and IL-10 may suppress the activity of pathogenic TH1 or Tc1 cells.

Heat shock proteins (hsps) are highly conserved proteins that play an important role in various cellular processes. Hsps are stress proteins that are typically upregulated during cellular stress. Apart from that, it has been shown that hsps are immunodominant. Those unique qualities of hsps (evolutionary conservation, immunodominance and upregulation during stress) have made hsps attractive candidates as targets for immunotherapy and vaccines. Indeed, at present, the role of immune reactivity to hsps has been proposed in different disease models, varying from cancer to infectious diseases and autoimmune diseases. Most evidence for the role of hsps in the immune regulation of inflammatory diseases comes from models of chronic arthritis. This research has shown that immunization with hsp10; hsp60 and hsp70 can all confer protection in virtually all models of experimental arthritis. In the model of adjuvant arthritis, immune reactivity to hsps plays a role both in the induction of disease and in protection from disease. On the one hand, it was shown that adjuvant arthritis can be induced by means of a T cell clone, called A2b, that is specific for mycobacterial hsp60 180–188. On the other hand, later studies showed that preimmunization with mycobacterial hsp60 can effectively protect against disease induction. However, after immunization with hsp60 several epitopes were found to be recognized by the immune system. Interestingly, only one epitope (mycobacterial hsp 60 256–270) out of eight epitopes was found to be capable to induce protection. This protection was based on the induction of (self-hsp) cross-reactive T cells. Thus arose a picture from the data of the animal model of adjuvant arthritis of an important role for immune reactivity against hsps in the regulation of arthritis, both in protection and in disease induction. The fact that different epitopes had completely opposite effects underlined the importance of defining peptide T cell epitopes, also in the human system.

Over the last 10 years it has become clear that immune reactivity to hsps also plays a crucial role in human chronic arthritis, namely Juvenile Idiopathic Arthritis (JIA) and Rheumatoid Arthritis (RA). First, an increased expression of hsp60 was detected in synovial lining cells of subjects with JIA and RA. Secondly, T cell reactivity to both self and non-self hsp60 was found in both diseases. Similarly immune reactivity to other hsps such as hsp70 and DnaJ was detected in subjects with JIA and RA. In children with JIA, immune reactivity to self-hsp60 seemed predictive of a favorable prognosis. Accordingly, modulation of inflammatory responses to hsps in immune-mediated diseases, ranging from auto-immunity to cancer to infectious diseases is desired.

SUMMARY OF THE INVENTION

The present invention overcomes many of the problems in the art by providing substantially pure HLA pan DR-binding peptides comprising a fragment of a stress protein that binds to MHC class II molecules.

In one embodiment, the invention provides methods for treating or preventing an immune-mediated disease in a subject having or at risk of having the disease including administering to the subject, an effective amount of a substantially pure peptide comprising a fragment of a stress protein that binds to one or more MHC class II molecules in a pharmaceutically acceptable carrier, wherein the peptide modulates an immune response, thereby treating or preventing the disease.

In another embodiment, the present invention provides a pharmaceutical composition, comprising one or more invention HLA pan DR-binding peptides in a pharmaceutically acceptable carrier.

In yet another embodiment, the present invention provides isolated nucleic acid sequences encoding the invention HLA pan DR-binding peptides.

In still another embodiment, the present invention provides methods for inducing an immune response in a subject comprising administering to the subject, an effective amount of a substantially pure HLA pan DR-binding peptide comprising a fragment of a stress protein that binds to an MHC class II molecule.

BRIEF DESCRIPTION OF THE DRAWINGS

FIG. 7A shows T cell proliferative responses: PBMC from patients (n=7) were stimulated for 5 days with 10 g/ml of dnaJP1 peptide. Evaluation was performed at monthly intervals. Controls include PHA as a general mitogen and dnaJpV. FIGS. 7B–E show evaluation by FACS at monthly intervals of production of intracellular cytokine (pro inflammatory: FIGS. 7B–D; tolerogenic: FIG. 7E) by PBMC of the patients who were responsive at the screening to dnaJP1 peptide. FIG. 7B: IL-2, n=6; FIG. 7C: IFN-γ, n=8; FIG. 7D: TNF-α, n=6; FIG. 7E: IL-4 and IL-10, n=4. Results are expressed as % CD3+cells in dnaJP1stimulated-unstimulated cultures. (*=p.<0.05)

FIG. 8A shows the number of tender joints; FIG. 8B shows the number of swollen joints. Measurments taken at monthly intervals. (*=p.<0.05)

DETAILED DESCRIPTION OF THE INVENTION

Figure 1:
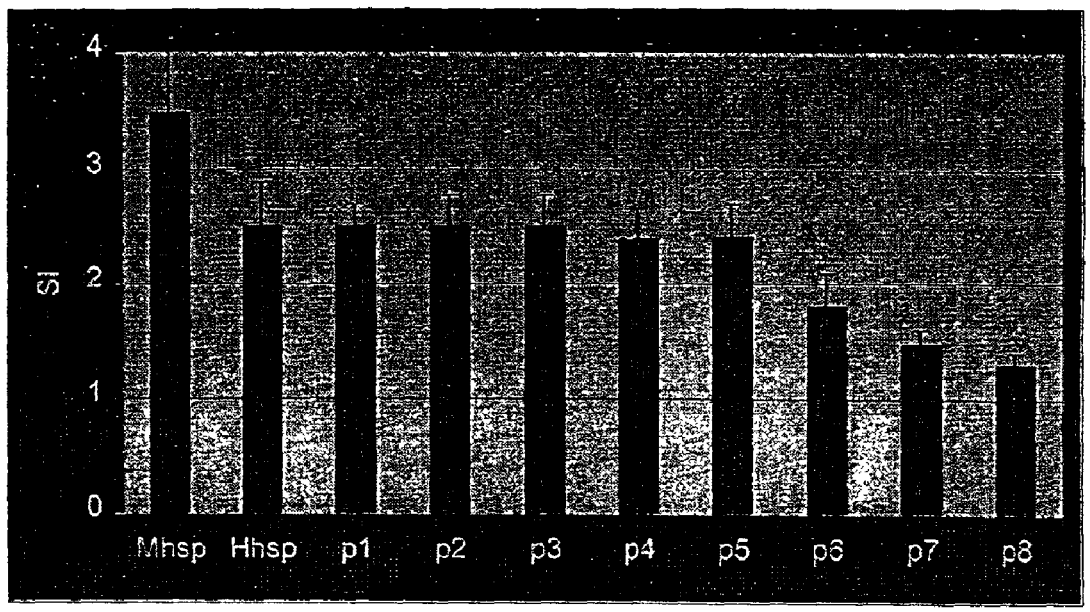
FIG. 1 shows the T cell proliferative response to pan DR binding hsp60 peptides in cells from 80 subjects with Juvenile Idiopathic Arthritis. On the Y-axis is shown the Stimulation Index (S) defined as the mean counts per minute (CPM) in wells with cells cultured with antigens, divided by the mean cpm in wells cultured with medium alone. The X-axis shows the different antigens tested in the assay: (from left to right) whole mycobacterial hsp60 (Mhsp), whole human hsp60 (Hhsp60), p1 (myc 254–268), p2 (hum 280–294), p3 (myc 216–230), p4 (hum 242–256), p5 (myc 210–224), p6 (hum 236–250), p7 (myc 503–517), and p8 (hum 535–546).

The present invention provides novel peptide sequences that modulate T cell responsiveness due to the promiscuous binding and presentation of the peptides with a variety of MHC molecules. In one embodiment, increased presentation of the peptides of the present invention results in an increased likelihood of immunological recognition and thus such peptides are ideal candidates for molecules that modulate immune response, such as vaccines and modulators of inflammatory reactions in which the immune response is downregulated, as well as cancer and infectious disease therapeutics in which the immune response is upregulated to augment the body's attack upon the aberrant cells.

The contradictory role of different epitopes of mycobacterial hsp60 in adjuvant arthritis, made it imperative to determine peptide T-cell epitopes of hsp60 in subjects with JIA and RA. Based on the data gathered in the animal models, various attempts were made to identify T cell epitopes in subjects with JIA. However, predictions on potential epitopes, based on data from the model of adjuvant arthritis, proved ineffective for the identifications of T cell epitopes in the human system. Especially in the case of JIA, the heterogenic HLA background of subjects with JIA hampered the prediction of potential T cell epitopes of hsp60. This made prediction based on MHC binding assays impossible and prediction based on theoretical optimal binding to DR4 worthless.

The present invention identifies promiscuous pan-DR T cell epitopes. These peptides fit in various different MHC molecules, especially MHC class II molecules, and thus are recognized by T cells in the vast majority of subjects. To identify the promiscuous pan-DR peptides, a computer algorithm described in U.S. Pat. No. 6,037,135 (incorporated herein by reference in its entirety) that identifies motifs for binding of peptides to various MHC class II molecules was used. Sequences of both mycobacterial and human hsp60 were scanned and based on the predicted binding of peptide sequences to three subtypes of HLADR, namely DR1, DR4 and DR7, peptides were designed (Table 1). The peptides were selected on the level of predicted binding to DR1, DR4 and DR7. The peptides of the present invention including those listed in Table 1, have been identified in in vitro tests as having the ability to induce the proliferation of autoreactive T cells or to induce the secretion of cytokines (e.g., lymphokines) from these T cells or to induce other effector functions such as cytotoxicity.

As discussed above, hsps are targets for the immune system during immune mediated chronic inflammation. More specifically, immune modulation using hsps based upon experimental models can provide novel therapeutics for diabetes, inflammatory bowel diseases, diabetes, arthritis and transplantation related diseases.

The present invention provides peptides and methods of using the novel peptides to modulate, block, or inhibit inflammatory responses. The peptides and methods are useful for screening peptides or peptide analogs that modulate (i.e., either down-regulate, up-regulate, or shift the ratio of TH1:TH2 molecules produced) the pathogenic immune response; to monitor efficacy or therapeutic use; and to identify other agents that may be effective to down-regulate or inhibit an immune response in treatment of such chronic inflammatory conditions.

Hsps are also targets for the immune system during immune mediated cancerous conditions and pathogenic infections. In this situation, immune modulation using hsps based upon experimental models can provide novel therapeutics for such cancerous conditions as melanoma, leukemia, lymphoma, solid tumours (lung, liver, kidney, brain, bladder), retinoblastoma, sarcomas and other connective tissue cancers, and the like. Immune-mediated pathogenic infections that can be treated using the invention HLA pan DR peptides include such immune mediated microbial infections as tuberculosis, leprosis, bacterial infections of Gram positive and Gram negative microroganisms, HIV/AIDS, Epstein BarrVirus and Cytomegalovirus infections, and protozoan infections, such as *Leishmania*, and the like.

The present invention provides peptides and methods of using the novel peptides to up-regulate the body's immune response so as to modulate, block, or inhibit precancerous or cancerous conditions and microbial infections. The peptides and methods are useful for screening peptides or peptide analogs that up regulate the body's immune response so as to counteract the progression of a cancerous condition or microbial infection; to monitor efficacy or therapeutic use of such peptides; and to identify other agents that may be effective to up-regulate or modulate an immune response in treatment of such immune-mediated precancerous or cancerous conditions and microbial infections.

The substantially pure HLA pan DR-binding peptides of the invention comprise a fragment of a stress protein that binds to an MHC class II molecule, for example, HLADR1, DR4 and DR7. The invention HLA pan DR-binding peptides can be derived, for example, from mycobacterial heat shock proteins (hsp60) and human heat shock proteins (hsp60).

Vertebrates possess the ability to mount an immune response as a defense against pathogens from the environment as well as against aberrant cells, such as tumor cells, which develop internally. This can take the form of innate immunity, which is mediated by NK cells, neutrophils and cells of the monocyte/macrophage lineage, or the form of acquired or active immunity against specific antigens mediated by lymphocytes. Active immune responses can be further subdivided into two arms, the humoral response which entails the production of specific antibodies that serve to neutralize antigens exposed to the systemic circulation and aid in their uptake by professional phagocytic cells, and the cellular arm which is required for recognition of infected or aberrant cells within the body.

In both cases, the specific response is regulated by the intracellular processing and recognition of the antigen by effector T-cells. Mature cytolytic T lymphocytes (CTLs) or T helper cells (Th), remain in a resting state unless they encounter antigens that their receptors can recognize in the context of MHC class I or II molecules. Upon encountering the specific antigens, the T-cells proliferate and perform effector functions, the result of which is elimination of the reactive antigens. When the antigen is processed through the cytoplasmic route, the resultant peptides are bound to nascent MHC class I molecules which facilitate appropriate presentation to effector T-cells. MHC class I presentation favors recognition by cytotoxic T lymphocytes (CTLs) that carry the CD8 ligand. In contrast, intracellular processing via the endocytic route results in presentation on MHC class II molecules, which mode of processing favors T helper responses involved in stimulation of the humoral arm. The goal of vaccination is to prime both responses and generate memory T cells, such that the immune system is primed to react to a pathogenic infection.

Activation of the T cells entails the generation of a series of chemical signals (primarily cytokines) that result in direct action or stimulating other cells of the immune system to act. In the case of activation by class I MHC-antigen, CTLs proliferate and act to destroy infected cells presenting that given antigen. Killing an infected cell prevents the virus from proliferating and makes it accessible to neutralizing antibodies, hence permitting elimination of the virus. In contrast, activation of Th cells by class II MHC-antigen complexes does not destroy the antigen presenting cell (which is part of the host's defense system) but rather stimulates the Th cell to proliferate and generate signals (again primarily cytokines) that affect various cells. Among other consequences, the signaling leads to B cell stimulation, macrophage activation, CTL differentiation and promotion of inflammation. This concerted response is relatively specific and is usually directed to foreign elements bearing the peptide presented by the class II MHC system.

When operating properly the immune response is surprisingly effective at eliminating microscopic pathogens and, to a lesser extent, neoplastic cells. In general, the complicated mechanisms for self-recognition are efficient and allow a strong response to be directed exclusively at foreign antigens. The regulation of self/non-self discrimination, which is a critical function of the immune system, involves multiple mechanisms during the development and life-span of T and B lymphocytes. Whereas deletion of self-reactive T and B cell precursors in the central lymphoid organs eliminates most of the autoreactive cells, the peripheral mechanisms that require Fas, IL-2R and CTLA-4 mediated signaling are thought to be crucial for immune homeostasis. Unfortunately, the immune system occasionally malfunctions and turns against the cells of the host, thereby provoking an autoimmune response. Autoimmunity or autoreactivity typically occurs when antigen receptors on immune cells recognize specific self-antigens (e.g., self-epitopes) on host cells and initiate reactions that result in the destruction of the host cells. In many cases, autoimmune reactions are self-limited in that they disappear when the antigens that provoked them are cleared away. However, in some instances the autoreactive lymphocytes survive longer than they should and continue to induce apoptosis or otherwise eliminate host cells. Examples of autoimmune disorders or conditions include multiple sclerosis (MS), rheumatoid arthritis (possibly more than one mechanism), lupus eythrematosis and type I diabetes.

Recent developments in the field, in particular the identification of allele specific peptide binding motifs, have transformed the field (Madden et al., 1991; Rotschke and Falk, 1991). Based on this knowledge, the structural basis for MHC linked susceptibility to autoimmune diseases can be reassessed at a level of detail sufficient for solving longstanding questions in the field. Motifs for peptide binding to several MHC class I and class II molecules have been defined by sequence analysis of naturally processed peptides and by mutational analysis of known epitopes. MHC class I bound peptides were found to be short (generally 8–10 amino acids long) and to possess two dominant MHC anchor residues; MHC class II bound peptides were found to be longer and more heterogeneous in size (Madden et al., 1991; Rotschke & Falk, 1991; Jardetzky et al. 1991, Chicz et al. 1993). More recently, a crystal structure for HLA-DR1 demonstrated that there is a dominant hydrophobic anchor residue close to the N-terminus of the peptide and that secondary anchor residues are found at several other peptide positions (Brown et al., 1993).

Heat shock proteins, which are included in the class known as stress proteins, useful in the practice of the instant invention can be selected from among any cellular protein that satisfies any one of the following criteria. A heat shock protein is characterized by having its intracellular concentration increase when a cell is exposed to a stressful stimuli, by being capable of binding other proteins or peptides, by being capable of releasing the bound proteins or peptides in the presence of adenosine triphosphate (ATP) or low pH, or by having at least 35% homology with any cellular protein having any of the above properties.

To date, three major families of hsps have been identified based on molecular weight. The families have been called hsp60, hsp70 and hsp90 where the numbers reflect the approximate molecular weight of the stress proteins in kilodaltons. Mammalian hsp90 and gp96 each are members of the hsp90 family. Many members of these families were found subsequently to be induced in response to other stressful stimuli including, but not limited to, nutrient deprivation, metabolic disruption, oxygen radicals, and infection with intracellular pathogens. (See Welch, May 1993, *Scientific American* 56–64; Young, 1990, *Annu. Rev. Immunol.* 8:401–420; Craig, 1993, *Science* 260:19021903; Gething, et al., 1992, *Nature* 355:33–45; and Lindquist, et al., 1988, *Annu. Rev. Genetics* 22:631–677), the disclosures of which are incorporated herein by reference. It is contemplated that hsps/stress proteins belonging to all of these three families can be used in the practice of the instant invention. In a preferred embodiment, an hsp60 protein and protein sequence is used to derive the peptides of the invention. Hsp60 proteins are abundant at normal temperatures in most, but not all, mammalian cells and are further induced by heat (Lai, et al., 1984, *Mol. Cell. Biol.* 4:2802–10; van Bergen en Henegouwen, et al., 1987, *Genes Dev.* 1:525–31).

Heat shock proteins are highly conserved proteins. For example, the hsp60 and hsp90 families show high levels of intra families conservation. In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. (See U.S. Pat. No. 5,961,979, which is incorporated herein by reference in its entirety.) The purification of stress proteins belonging to these three families is described below.

In one embodiment, the hsp used in accordance with the invention is a mammalian hsp. In another embodiment, the hsp used in accordance with the invention for the treatment of autoimmune disease is a member of the hsp60 family.

The 60 kDa heat shock protein (hsp60) is a stress protein expressible in all of the cells of the body. Nevertheless, healthy individuals manifest a high frequency of autoimmune T cells specific for hsp60 self-epitopes. Normal healthy mice and humans have been shown to have T cells targeted at their self hsp60 antigen (Kaufmann, 1990; Kaufmann et al., 1994; Young, 1989; Cohen, 1992b). However, these autoimmune T cells are also involved in T cell mediated autoimmune diseases: a high concentration of T cells targeted at self hsp60 antigen have been found in the autoimmune lesions of human chronic arthritis (Cohen, 1991; Res et al., 1989; van Eden et al., 1989), multiple sclerosis (Selmaj et al., 1991), experimental autoimmune encephalomyelitis (Selmaj et al., 1991) and adjuvant arthritis (Hogervorst et al., 1992). Anti-hsp60 T-cells have also been shown to play a role in diabetes mellitus in the non-obese diabetic (NOD) mouse model (Elias et al., 1990; Elias et al., 1991; Elias et al., 1994; Elias et al., 1995; Birk et al., 1996a; Birk et al., 1993; Cohen, 1991).

HLA pan DR binding peptides of the invention have an amino acid sequence that is conserved in the corresponding heat shock proteins between humans and other lower organisms, particularly between human and bacterial or human and mycobacterial heat shock proteins, such as hsp60 and dnaJ respectively.

The term "isolated" or "purified" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated" or "purified", but the same polynucleotide or polypeptide separated from the coexisting materials of its natural state is "isolated" or "purified", as the term is employed herein.

A "substantially pure peptide" is typically pure when it is at least 60%, by weight, free from the proteins and naturally-occurring organic molecules with which it is naturally associated. Preferably, the preparation is at least 75%, more preferably at least 90%, and most preferably at least 99%, by weight, and has a sequence which is a fragment of the sequence as set forth in SEQ ID NO:1 or SEQ ID NO:13 (e.g., SEQ ID Nos: 2, 3, 4, 5, 6, 7, 8, 9, 10) A substantially pure hsp60 peptide of the invention may be obtained, for example, by extraction from a natural source, by expression of a recombinant nucleic acid encoding a full-length polypeptide (e.g, SEQ ID NO:1 or SEQ ID NO:13), followed by cleavage with a protease; by expression of a recombinant nucleic acid encoding a fragment of SEQ ID NO:1 or SEQ ID NO:13 (e.g., SEQ ID Nos: 2, 3, 4, 5, 6, 7, 8, 9, or 10); or by chemically synthesizing the peptides of the invention. Purity can be measured by any appropriate method, e.g., by column chromatography, polyacrylamide gel electrophoresis, or by HPLC analysis.

Heat shock protein-60 (hsp60) peptides of the invention include fragments of the sequence as set forth in SEQ ID NO:1 Examples of invention fragments (i.e., peptides) of the hsp60 heat shock protein include the peptides having the sequences as set forth in Table 1 (P1, 2, 3, 4, 5, 6, 7, and 8 are SEQ ID Nos:2, 3, 4, 5, 6, 7, 8, and 9, respectively). Heat shock protein dnaJ peptides of the invention include fragments of the sequence as set forth in SEQ ID NO:14, such as peptides having the sequences of SEQ ID No: 10. Such peptides or polypeptides of the invention may be substantially purified.

TABLE 1

| Myc/Hum | Hsp60 | Sequence (SEQ ID Nos:2–9) | Core epitope (SEQ ID Nos:14–23) | DR1 score | DR4 score | DR7 score | Pan DR score |
|---|---|---|---|---|---|---|---|
| P1 MYC | 254–268 | GEALSTLVVNKIRGT | LSTLVVNKI | 42.37 | 17.03 | 276.91 | 3 |
| P2 HUM | 280–294 | GEALSTLVLNRLKVG | LSTLVLNRL | 12.46 | .94 | 8.74 | 1 |
| P3 MYC | 216–230 | PYILLVSSKVSTVKD | LVSSKVSTV | 3.59 | 14.29 | 26.68 | 3 |
|  |  |  | YILLVSSKV | 131.96 | 4.19 | 29.83 | 3 |
| P4 HUM | 242–256 | AYVLLSEKKISSIQS | LSEKKISSI | .17 | 2.82 | 7.94 | 1 |
| P5 MYC | 210–224 | EAVLEDPYILLVSSK | LEDPYILLV | 28.51 | .37 | 15.45 | 2 |
| P6 HUM | 236–250 | KCEFQDAYVLLSEKK | FQDAYVLLS | 40.82 | 3.63 | 96.80 | 3 |
| P7 MYC | 503–517 | IAGLFLTTEAVVADK | LTTEAVVAD | 1.76 | .28 | 3.66 | 1 |
|  |  |  | FLTTEAVVA | 10.51 | 1.28 | 18.65 | 2 |
| P8 HUM | 535–546 | VASLLTTAEVVVTEI | LTTAEVVVT | 12.03 | 3.34 | 68.00 | 3 |

Table 1 shows a set of hsp60 peptides selected on DR binding. The table shows (from left to right) the number of the peptide; the origin (human or mycobacterial), the peptide composition (in bold the core epitope); the core epitope; predicted binding to DR1, DR4, DR7; and the pan DR score. The cut off points for considering an epitope to be a good binder were as follows: DR1~1.570; DR4~2.617, DR7~9.106.

A polypeptide, peptide, or protein refers to a polymer in which the monomers are amino acid residues which are joined together through amide bonds. When the amino acids are alpha-amino acids, either the L-optical isomer or the D-optical isomer can be used, the L-isomers being typical. A peptide of the invention is intended to encompass a fragment of SEQ ID NO:1. Specific examples of fragments of SEQ ID NO:1 or SEQ ID NO:13 encompassed by the present invention include the sequence as set forth in SEQ ID Nos:2, 3, 4, 5, 6, 7, 8, 9, or 10, comprised of L- or D-amino acids and include modified sequences such as glycoproteins. Accordingly, the peptides of the invention are intended to cover naturally occurring proteins, as well as those which are recombinantly or synthetically synthesized. Also encompassed by the present invention are peptides having substantially the same sequence as SEQ ID Nos:2, 3, 4, 5, 6, 7, 8, 9, or 10 and which peptides retain a functional activity of the sequence to which it is related. Peptides having substantially the same sequence can be designed based upon conservative amino acid substitutions that would still have an approximately 70%–90% homology to the original peptide over the corresponding portion. A yet greater degree of departure from homology is allowed if like-amino acids, i.e. conservative amino acid substitutions, do not count as a change in the sequence. The peptides are about 10–30 amino acids in length; preferably 15–25 amino acids and more particularly 15–20 amino acids in length.

A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on.

"Salts" of the hsp60 peptides of the invention contemplated by the invention are physiologically acceptable organic and inorganic salts.

"Functional derivatives" of the hsp60 peptides as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof.

These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for examples that of seryl or threonyl residues) formed by reaction with acyl moieties.

Sequencing algorithms can be used to measure homology or identity between known and unknown sequences. Such methods and algorithms are useful in identifying corresponding sequences present in other organisms as well as in the design of peptides of the invention. Homology or identity is often measured using sequence analysis software (e.g, Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids, polypeptide, or peptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 8 to 10, 10 to 20, 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, *Adv. Appl. Math*. 2:482 (1981), by the homology alignment algorithm of Needleman & Wunsch, *J. Mol. Biol* 48:443 (1970), by the search for similarity method of person & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is BLAST and BLAST 2.0 algorithms, which are described in Altschul et al., *Nuc. Acids Res*. 25:3389–3402 (1977) and Altschul et al., *J. Mol. Biol*. 215:403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0).

For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) or 11, an expectation (E) or 10, M=5, N=4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=4, and a comparison of both strands.

The BLAST algorithm also performs a statistical analysis of the similarity between two sequences (see, e.g., Karlin & Altschul, *Proc. Natl. Acad. Sci. USA* 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, http://weber.u.Washington.edu/~roach/human_genome_progress2.html) (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al, 1997), and *D. melanogaster* (Adams et al., 2000). Significant progress has also been made in sequencing the genomes of model organism, such as mouse, *C. elegans, Arabadopsis sp*. and *D. melanogaster*. Several databases containing genomic information annotated with some functional information are maintained by different organization, and are accessible via the internet, for example, http://wwwtigr.org/tdb; http://www.genetics.wisc.edu; http://genome-www.stanford.edu/~ball; http://hiv-web.lanl.gov; http://www.ncbi.nlm.nih.gov; http://www.ebi.ac.uk; http://Pasteur.fr/other/biology; and http://www.genome.wi.mit.edu.

In addition to peptides of the invention, nucleic acid sequences (e.g., oligonucleotide or polynucleotide sequences) encoding fragments of SEQ ID NO:1 or SEQ ID NO:13 (e.g., SEQ ID Nos:2, 3, 4, 5, 6, 7, 8, 9, or 10) are encompassed by the present invention. For example, DNA sequences of the invention can be obtained by several methods. For example, the nucleic acid (e.g., DNA or RNA) sequence can be derived for SEQ ID Nos:2, 3, 4, 5, 6, 7, 8, 9, or 10 or 12 based upon the degeneracy of the genetic code and determined using computer based algorithms and sequence programs. There are 20 natural amino acids, most of which are specified by more than one codon. Therefore, all degenerate nucleotide sequences are included in the invention so long as the amino acid sequence of a peptide of the invention encoded by the nucleic acid sequence is functionally unchanged.

Polynucleotide, oligonucleotide, or nucleic acid sequence refers to a polymeric form of nucleotides and are used interchangeably herein. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

The nucleic acid sequence (e.g., an oligonucleotide or a polynucleotide) encoding a peptide of the invention, includes complementary polynucleotide sequences. When the sequence is RNA, the deoxyribonucleotides A, G, C, and T are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes a polypeptide or peptide sequence of the invention. "Selective hybridization" as used herein refers to hybridization under moderately stringent or highly stringent physiological conditions (See, for example, the techniques described in Maniatis et al, 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Screening procedures which rely on nucleic acid hybridization make it possible to isolate any gene sequence from any organism, provided the appropriate probe is available. For example, it is envisioned that such probes can be used to identify other homologs in other organisms. In accomplishing this, alignment algorithms (as described above) can be used to screen genome databases. Alternatively, oligonucleotide probes, which correspond to a part of the sequence encoding the protein in question, can be synthesized chemically. This requires that short, oligopeptide stretches of amino acid sequence must be known (e.g., SEQ ID Nos:2, 3, 4, 5, 6, 7, 8, 9, or 10). The DNA sequence encoding the protein can be deduced from the genetic code, however, the degeneracy of the code must be taken into account.

In the invention, a nucleic acid sequences encoding SEQ ID Nos:2, 3, 4, 5, 6, 7, 8, 9, or 10 may be inserted into a recombinant expression vector. The term "recombinant expression vector" refers to a plasmid, virus or other vehicle known in the art that has been manipulated by insertion or incorporation of a nucleic acid sequence encoding SEQ ID Nos:2, 3, 4, 5, 6, 7, 8, 9, or 10. Such expression vectors contain a promoter sequence which facilitates the efficient transcription of the inserted genetic sequence. The expression vector typically contains an origin of replication, a promoter, as well as specific genes which allow phenotypic selection of a transformed cell(s). Vectors suitable for use in the present invention include those described herein.

Methods, which are well known to those skilled in the art, can be used to construct expression vectors containing sequences encoding, for example, SEQ ID Nos:2, 3, 4, 5, 6, 7, 8 ,9, or 10 and appropriate transcriptional/translational control signals. These methods include in vitro recombinant DNA techniques, synthetic techniques, and in vivo recombination/genetic techniques. (See, for example, the techniques described in Maniatis et al., 1989, *Molecular Cloning A Laboratory Manual*, Cold Spring Harbor Laboratory, N.Y.).

The genetic construct can be designed to provide additional benefits, such as, for example addition of C-terminal or N-terminal amino acid residues that would facilitate purification by trapping on columns or by use of antibodies. All those methodologies are cumulative. The choice as to the method of producing a particular construct can easily be made by one skilled in the art based on practical considerations: size of the desired peptide, availability and cost of starting materials, and the like. All the technologies involved are well established and well known in the art. See, for example, Ausubel et al., *Current Protocols in Molecular Biology*, Volumes 1 and 2 (1987), with supplements, and Maniatis et al., *Molecular Cloning, a Laboratory Manual*, Cold Spring Harbor Laboratory (1989). Yet other technical references are known and easily accessible to one skilled in the art.

Nucleic acid sequences can be created which encode a fusion protein and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired product. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a peptide or protein-encoding nucleic acid sequence, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the nucleic acid sequence. Both constitutive and inducible promoters, are included in the invention (see e.g., Bitter et al., *Methods in Enzymology* 153:516–544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a nucleic acid sequence encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a nucleic acid sequence encoding a peptide having, for example, a sequence as set forth in SEQ ID Nos:2, 3, 4, 5, 6, 7, 8, 9, or 10. The expression vector typically contains an origin of replication, a promoter, as well as specific genes which allow phenotypic selection of the transformed cells. Vectors suitable for use in the invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a nucleic acid sequence encoding a peptide of the invention such that the localization or signal peptide is located at the amino terminal end of a resulting encoded fusion polypeptide. The construction of expression vectors and the expression of genes in transfected cells involves the use of molecular cloning techniques also well known in the art. (See, for example, Sambrook et al, *Molecular Cloning—A Laboratory Manual*, Cold Spring Harbor Laboratory, Cold Spring Harbor, N.Y., 1989, and *Current Protocols in Molecular Biology*, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., *Molecular Cloning A Laboratory Manual*, Cold Spring Harbor Laboratory, N.Y., 1989).

In yeast, a number of vectors containing constitutive or inducible promoters may be used. For a review see, *Current Protocols in Molecular Biology*, Vol. 2, Ed. Ausubel, et al., Greene Publish. Assoc. & Wiley Interscience, Ch. 13, 1988; Grant, et al., "Expression and Secretion Vectors for Yeast," in *Methods in Enzymology*, Eds. Wu & Grossman, 1987, Acad. Press, N.Y., Vol. 153, pp.516–544, 1987; Glover, *DNA Cloning*, Vol. II, IRL Press, Wash., D.C., Ch. 3, 1986; and Bitter, "Heterologous Gene Expression in Yeast," *Methods in Enzymology*, Eds. Berger & Kimmel, Acad. Press, N.Y., Vol. 152, pp. 673–684, 1987; and *The Molecular Biology of the Yeast Saccharomyces*, Eds. Strathem et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: *DNA Cloning* Vol. 11, *A Practical Approach*, Ed. D M Glover, IRL Press, Wash., D.C., 1986).

Alternatively, vectors may be used which promote integration of foreign DNA sequences into the yeast chromosome.

An alternative expression system which could be used to express a peptide having, for example, a sequence as set forth in SEQ ID Nos:2, 3, 4, 5, 6, 7, 8, 9, or 10 is an insect system. In one such system, *Autographa californica* nuclear polyhedrosis virus (AcNPV) is used as a vector to express foreign or mutated sequences. The virus grows in *Spodoptera frugiperda* cells. The sequence encoding a peptide of the invention may be cloned into non-essential regions (for example, the polyhedrin gene) of the virus and placed under control of an AcNPV promoter (for example the polyhedrin promoter). Successful insertion of the sequences coding for a peptide of the invention will result in inactivation of the polyhedrin gene and production of non-occluded recombinant virus (i.e., virus lacking the proteinaceous coat coded for by the polyhedrin gene). These recombinant viruses are then used to infect *S. frugiperda* cells in which the inserted gene is expressed, see Smith, et al., *J. Viol.* 46:584, 1983; Smith, U.S. Pat. No. 4,215,051.

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a DNA molecule encoding a peptide of the invention, or analog thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in virus vectors and the like, as well as others known in the art, may be used. Eukaryotic cells can be cotransfected with DNA sequences encoding a peptide of the invention and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., *Drosophila sp.*) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and W138.

Mammalian cell systems which utilize recombinant viruses or viral elements to direct expression may be engineered. For example, when using adenovirus expression vectors, a nucleic acid sequence encoding a peptide of the invention may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a peptide of the invention in infected hosts (e.g., see Logan & Shenk, *Proc. Natl. Acad. Sci. USA*, 81:3655–3659, 1984). Alternatively, the vaccinia virus 7.5K promoter may be used. (e.g, see, Mackett, et al., *Proc. Natl. Acad. Sci. USA*, 79:7415–7419, 1982; Mackett, et al., *J. Virol.* 49:857–864, 1984; Panicali, et al., *Proc. Natl. Acad. Sci USA* 79:4927–4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a gene in host cells (Cone & Mulligan, *Proc. Natl. Acad. Sci. USA*, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the DNA encoding a peptide of the invention (e.g., a peptide having a sequence as set forth in SEQ ID Nos:2, 3, 4, 5, 6, 7, 8, 9, or 10) controlled by appropriate expression control elements (e.g., promoter, enhancer, sequences, transcription terminators, polyadenylation sites, and the like), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including, but not limited to, the herpes simplex virus thymidine kinase (Wigler, et al., *Cell*, 11:223, 1977), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., *Cell*, 22:817, 1980) genes can be employed in tk-, hgprt- or aprt- cells respectively. Also, anti-metabolite resistance can be used as the basis of selection for dhfr, which confers resistance to methotrexate (Wigler, et al., *Proc. Natl. Acad. Sci. USA*, 77:3567, 1980; O'Hare, et al., *Proc. Natl. Acad Sci. USA*, 8:1527, 1981); gpt, which confers resistance to mycophenolic acid (Mulligan & Berg, *Proc. Natl. Acad. Sci. USA*, 78:2072, 1981; neo, which confers resistance to the aminoglycoside G-418 (Colberre-Garapin, et al., *J. Mol. Biol.* 150:1, 1981), and hygro, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology*, Cold Spring Harbor Laboratory, ed., 1987).

In another embodiment, the invention provides antibodies that specifically bind to a peptide of the invention (e.g., SEQ ID Nos:2, 3, 4, 5, 6, 7, 8, 9, or 10). For example, an antibody that specifically binds to a peptide having a sequence of SEQ ID NO:2 does not bind to a peptide having a sequence of SEQ ID NO:4. If the peptide is glycosylated, the glycosylation pattern can be utilized as part of a purification scheme via, for example, lectin chromatography. Such antibodies are useful for research and diagnostics in the study of inflammatory disorders and diseases (e.g., rheumatoid arthritis, diabetes, and the like), and associated pathologies in general.

Such antibodies may be administered alone or contained in a pharmaceutical composition comprising antibodies that specifically bind to a sequence as set forth in SEQ ID Nos:2, 3, 4, 5, 6, 7, 8, 9, or 10 and other reagents effective as modulators of inflammatory reactions in vitro and in vivo.

The term "epitope", as used herein, refers to an antigenic determinant on an antigen, such as a peptide having a sequence as set forth in SEQ ID Nos:2, 3, 4, 5, 6, 7, 8, 9, or 10 to which the paratope of an antibody, such as an antibody that specifically binds to a sequence as set forth in SEQ ID Nos:2, 3, 4, 5, 6, 7, 8, 9, or 10 of the invention. Antigenic determinants usually consist of chemically active surface groupings of molecules, such as amino acids or sugar side chains, and can have specific three-dimensional structural characteristics, as well as specific charge characteristics.

Antibodies which bind to a peptide of the invention can be prepared using an intact peptides or fragments (e.g., fragments of SEQ ID NO:1 or SEQ ID NO:13) corresponding to the sequences of the peptides of the invention) containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Antibodies of the invention include polyclonal antibodies, monoclonal antibodies, and fragments of polyclonal and monoclonal antibodies.

The preparation of polyclonal antibodies is well-known to those skilled in the art. See, for example, Green et al., Production of Polyclonal Antisera, in *Immunochemical Protocols* (Manson, ed.), pages 1–5 (Humana Press 1992); Coligan et al., Production of Polyclonal Antisera in Rabbits, Rats, Mice and Hamsters, in *Current Protocols in Immunology*, section 2.4.1 (1992), which are hereby incorporated by reference.

The preparation of monoclonal antibodies likewise is conventional. See, for example, Kohler & Milstein, *Nature*, 256:495 (1975); Coligan et al., sections 2.5.1–2.6.7; and Harlow et al., *Antibodies: A Laboratory Manual*, page 726 (Cold Spring Harbor Pub. 1988), which are hereby incorporated by reference. Alternatively, an antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA*, 86:3833 (1989), which is hereby incorporated in its entirety by reference. Techniques for producing humanized monoclonal antibodies are described, for example, by Jones et al., *Nature*, 321:522 (1986); Riechmann et al., *Nature*, 332:323 (1988); Verhoeyen et al., *Science*, 239:1534 (1988); Carter et al., *Proc. Nat'l Acad. Sci. USA*, 89:4285 (1992); Sandhu, *Crit. Rev. Biotech.*, 12:437 (1992); and Singer et al., *J. Immunol.*, 150:2844 (1993), which are hereby incorporated by reference.

In another embodiment, the invention provides for the generation of autoreactive cells with the ability to recognize organ specific antigens and to produce mediators that suppress the activity of pathogenic cells instead of having the potential to promote disease. For example, it is desirable to selectively stimulate the production of immunomodulator compounds such as, for example, cytokines like IL-4, IL-10, IL-9, IL-13 and TGF-β. It will be appreciated that the induction of such immunomodulator compounds may be associated with the identity of the selected epitope in the context of the T cell repertoire, the cytokine context during priming and the inoculation regimen. Significantly, it will be appreciated that such a strategy is not limited to antigens that are central to the pathogenesis of an autoimmune disease, but potentially employs any organ-specific antigen. As such, selective induction of such immunomodulator compounds has several advantages in the amelioration of autoimmune disorders. For example, such a treatment does not require identification of the those epitopes that trigger the pathogenesis rather it may offer broad-based bystander suppression of T cells reactive against various epitopes. Moreover such a strategy would limit the risk of exacerbating the disease due to transient activation phase of pathogenic T cells during antigen therapy and it may circumvent the refractoriness of pathogenic T cells to peripheral tolerance mechanisms mediating anergy and deletion.

In another embodiment, the peptides of the invention are used as immunological agents in a pharmaceutical composition administered to modulate (e.g., prevent or suppress) an immune-mediated disease (i.e., a disease associated with an immune response). Accordingly, the peptides of the invention are intended to encompass salts and functional derivatives thereof, as well as hsp60 peptide analogs, so long as the biological activity of the protein or peptide with respect to modulating immune-mediated disease (i.e., a disease associated with an immune response)s is maintained.

Peptides of the invention (e.g., a peptide having a sequence as set forth in SEQ ID Nos:2, 3, 4, 5, 6, 7, 8, 9 or 10) are preferably administered prior to development of an immune-mediated disease in a subject at risk thereof. The term "prior to" is intended to mean a period of time during which a reaction based upon hsp60 autoimmunity is modulated by such treatment in the host, preferably at a time such that the optimal modulation (e.g., down-regulation) coincides with the time of the inflammatory reaction. Alternatively, a peptide of the invention can be administered in conjunction with another anti-inflammatory agent, such as an anti-inflammatory cytokine or an anti-TNFα agent.

In the present invention, administration of the pharmaceutical composition containing hsp60 peptides, or analogs thereof, as immunologically active agents to modulate inflammation in a subject can be through various routes known in the art, such as topically, orally, intranasally, intravenously, intramuscularly, or subcutaneously. Preferred modes of administration are intravenously, which is known to induce tolerance, or orally or intranasally, which are known to induce a TH1→TH2 shift. The preferred dosage of the peptides of the invention, or analogs thereof, will depend upon a number of factors including the type of disease, the age and weight of the subject, as well as the severity of the symptoms. One of skill in the art, can determine the proper dose empirically. For example, an optimum dosage and regimen can be determined by those of skill in the art by measuring for a shift from TH1 cytokine response to a TH2 cytokine response.

Peptides of the invention, or analogs thereof, may be given during or after an immunological or inflammatory reaction to further modulate (e.g., reduce or down-regulate) the inflammatory reaction. Inflammatory reactions applicable to the methods and compositions of the invention include, for example, autoimmune disease or disorders (e.g., insulin dependent diabetes mellitus (IDDM), multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, inflammatory bowel disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease). The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

The methods of the present invention can be used to treat such autoimmune-mediated diseases and inflammatory diseases or disorders by modulating (e.g., reducing or eliminating) the immune response to the subject's own (self) tissue, or, alternatively, by reducing or eliminating a pre-existing autoimmune response directed at tissues or organs transplanted to replace self tissues or organs damaged by the autoimmune response.

The administration of one or more peptides of the invention (e.g., peptides having sequences as set forth in SEQ ID Nos:2, 3, 4, 5, 6, 7, 8, 9 or 10) is preferably concomitant with the administration of conventional anti-inflammatory or immunosuppresive therapy.

It is expected that different epitopes of the hsp60 protein, such as those presented in Table 1 (e.g., SEQ ID Nos:2, 3, 4, 5, 6, 7, 8, 9 or 10), may be more effective in inflammatory responses in different individuals. Thus, the peptides of the invention can be screened against peripheral blood lymphocytes of the intended subject to see which peptide has the optimum effect on inflammation. For example, class II MHC molecules bind to peptides 12–15 amino acid residues in length (e.g., as short as 9 amino acid residues), and that class I MHC molecules bind peptides of 7–9 amino acid residues. Thus, peptide fragments of hsp60, such as those presented in Table 1, can be readily screened to determine one or more optimal peptides that can be administered to a particular individual subject, or to a subject of a given HLA-type, to modulate the individual's immune response, for example, to shift to a TH2 cytokine response and thereby down-regulate his/her inflammation.

Peripheral blood lymphocytes (PBL) of an individual human subject can be isolated from whole blood by Ficoll-Hypaque density gradient centrifugation as is well-known in the art. This sample of the subject's lymphocytes can be tested for binding to the peptides to be screened in accordance with the method disclosed in Mozes et al., U.S. Pat. No. 5,356,779, or can be tested for in vitro T-cell proliferation and subsequent T-cell cytokine response as assays to determine an optimal or near optimal peptide sequence for a specific individual subject.

Another way to screen a panel of peptides is to test the subject's lymphocytes for in vitro proliferation in the presence of each of the peptides of the panel or to test for TH1→TH2 shift caused by such peptides. Thus, supernatants of T-cells cultured with test peptides at concentrations of 5–50 ug/ml may be collected at different time points and tested for the activity of various cytokines, such as IFNγ and IL-4 secreted into the culture medium, which can be quantitated by ELISA using standard ELISA protocols, or for the presence of antibodies of particular classes. TH1 cells secrete cytokines which induce T cell proliferation, and cytokines such as IFNγ, which mediate tissue inflammation. On the other hand, TH2 cells secrete IL-4, which helps β-cells secrete antibodies of the IgG and IgE class and suppress the production of TH1 inflammatory cytokines, as well as IL-10, which indirectly inhibits TH1 activation by affecting antigen presentation and inflammatory cytokine production by macrophages. Accordingly, a measurement of the cytokine profile of the in vitro proliferated T cells will also be an indication of a shift from a TH1 T cell response to a TH2 T cell response. Thus, the TH1→TH2 shift can serve as a marker for monitoring the in vitro response of a subject's T lymphocytes to various test peptides in determining optimal or near optimal peptides.

The therapeutic regimens and pharmaceutical compositions of the invention can be used with additional immune response enhancers or biological response modifiers including, but not limited to, the cytokines IFN-α, IFN-γ, IL-2, IL-4, IL-6, TNF, or other cytokine affecting immune cells.

One or more peptides of the invention can be administered, for in vivo application, mucosally (e.g. by suppository, inhaler or orally), parenterally by injection, or by gradual perfusion over time. Administration may be orally, intravenously, intraperitoneally, intramuscularly, subcutaneously, intracavity, or transdermally. One or more peptides of the invention can also be co-administered with with an adjuvant, hormone, cytokine, corticosteroid, or the like. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobial, anti-oxidants, chelating agents and inert gases and the like.

It is envisioned that the invention can be used to treat pathologies associated with immune-mediated disorders, such as inflammation and autoimmune disorders, pathogenic infections and cancerous or precancerous conditions, by modulating an immune response in the treated subject. Therefore, the present invention encompasses methods for ameliorating a disorder associated with immune-mediated diseases, including those associated with an antigen-specific immune response to a self-antigen. The invention methods include treating a subject having the disorder or disease condition, at the site of the disorder or condition, with one or more peptides of the invention having, for example, a sequence as set forth in SEQ ID Nos:2, 3, 4, 5, 6, 7, 8, 9, or 10, or an analog thereof. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for an infection or disease and/or adverse effect attributable to the infection or disease. "Treating" as used herein covers any treatment of, or prevention of a disease in a vertebrate, a mammal, particularly a human, and includes: (a) preventing the disorder from occurring in a subject that may be predisposed to the disorder, but has not yet been diagnosed as having it; (b) inhibiting the disorder, i.e., arresting its development; (c) relieving or ameliorating the disorder, i.e., causing regression of the disorder or, (d) modulating an ongoing immune response that mediates the disorder so as to counteract the progression of the condition or disorder.

The invention includes various pharmaceutical compositions useful for ameliorating symptoms attributable to an immune-mediated disorders, as describe herein. The pharmaceutical compositions according to one embodiment of the invention are prepared by bringing an antibody against a peptide having a sequence selected from the group consisting of SEQ ID Nos:2, 3, 4, 5, 6, 7, 8, 9, or 10, a peptide analog of the foregoing sequences, a peptide mimetic of the foregoing, a drug, chemical or combination of chemicals or an agent that modulates the biological activity of the peptides of invention, into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co., 1405–1412, 1461–1487 (1975) and *The National Formulary XIV.*, 14th ed. Washington: American Pharmaceutical Association (1975), the contents of which are hereby incorporated by reference. The pH and exact concentration of the various components of the pharmaceutical composition are adjusted according to routine skills in the art. See *Goodman and Gilman's The Pharmacological Basis for Therapeutics* (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science*, 249:1527, (1990); Gilman et al. (eds.) (1990), each of which is herein incorporated by reference.

In one embodiment, the invention provides a pharmaceutical composition useful for administering a peptide of the invention, an analog thereof, or a nucleic acid encoding a peptide of the invention, to a subject in need of such treatment. "Administering" the pharmaceutical composition of the present invention may be accomplished by any means known to the skilled artisan. Preferably a "subject" refers to a mammal, most preferably a human, but may be any organism.

A peptide or antibody of the invention can be administered orally, parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

Another delivery system for nucleic acid and peptide sequences of the invention is a colloidal dispersion system. Colloidal dispersion systems include macromolecule complexes, nanocapsules, microspheres, beads, and the like.

In another embodiment, the invention provides a method for identifying an agent which interacts with or modulates the activity of an hsp60 protein or the biological activity of a peptide of the invention including incubating components comprising an agent and a peptide of the invention (e.g., a peptide having a sequence as set forth in SEQ ID Nos:2, 3, 4, 5, 6, 7, 8, 9 or 10), or a recombinant cell expressing a such a peptide, under conditions sufficient to allow the agent to interact and determining the affect of the agent on the activity of the polypeptide or peptide. The term "affect", as used herein, encompasses any means by which a peptide's activity can be modulated, and includes measuring the interaction of the agent with the peptide by physical means including, for example, fluorescence detection of the binding of the agent to the peptide. "Agents" can include, for example, polypeptides, peptidomimetics, chemical compounds, small molecules and biologic agents as described herein.

Incubating includes conditions which allow contact between the test agent and a peptide of the invention, or a cell expressing a peptide of the invention. Contacting includes in solution and in solid phase. The test agent may optionally be a combinatorial library for screening a plurality of agents. Agents identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Areas of investigation are the development of therapeutic treatments. The screening identifies agents that modulate the biological activity of a peptide of the invention in targeted organisms. Of particular interest are screening assays for agents that have a low toxicity or a reduced number of side effects for humans.

The term "agent" as used herein describes any molecule, e.g protein or pharmaceutical, with the capability of altering or mimicking the physiological function or expression of a peptide having a sequence as set forth in SEQ ID Nos:2, 3, 4, 5, 6, 7, 8, 9, or 10). Generally, a plurality of assay mixtures are run in parallel with different agent concentrations to obtain a differential response to the various concentrations. Typically, one of these concentrations serves as a negative control, i.e. at zero concentration or below the level of detection.

In another embodiment, the invention provides a method for identifying an agent which modulates (e.g., inhibiting) an hsp60-associated disorder (e.g., an inflammatory disorder or disease) by administering to a cell or subject having the hsp60-associated disorder an effective amount of a composition which contains a peptide of the invention, or an analog thereof, or an agent (e.g, an antibody, ribozyme, antisense molecule, or double-stranded interfering RNA molecules) that interacts with or inhibits the symptoms of the hsp60 associated disorder. Symptom can include, for example, the production of cytokines as identified herein, TH1 and TH2 responses, as well as pathologies associated with inflammation (e.g., swelling, vasodilation and the like).

Detection of hsp60 or dnaJP1 Polypeptides in Vivo and in Vitro

In a further embodiment, the invention provides a method of detecting an hsp60 polypeptide in a subject including contacting a cell component containing or suspected of containing an hsp60 or dnaJP1 polypeptide with a reagent (e.g., an antibody that specifically binds to a peptide sequence as set forth in SEQ ID Nos:2, 3, 4, 5, 6, 7, 8, 9 or 10) which binds to the cell polypeptide (herein after cell component). The cell component may contain in addition to hsp60 or danJP1 polypeptide, a nucleic acid, such as DNA or RNA. When the cell component is protein, the reagent is typically an antibody probe. The probes are detectably labeled, for example, with a radioisotope, a fluorescent compound, a bioluminescent compound, a chemiluminescent compound, a metal chelator or an enzyme. Those of ordinary skill in the art will know of other labels suitable for binding to an antibody or nucleic acid probe, or will be able to ascertain such, using routine experimentation. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

A monoclonal antibody of the invention, directed toward a peptide of the invention (e.g, a peptide having a sequence as set forth in SEQ ID Nos:2, 3, 4, 5, 6, 7, 8, 9 or 10) is useful for the in vivo and in vitro detection of antigen. The detectably labeled monoclonal antibody is given in a dose which is diagnostically effective. The term "diagnostically effective" means that the amount of detectably labeled monoclonal antibody is administered in sufficient quantity to enable detection of a proteins or polypeptide antigen for which the monoclonal antibodies are specific.

The concentration of a detectably labeled monoclonal antibody administered to a subject should be sufficient such that the binding to those cells, body fluid, or tissue having an hsp60 polypeptide sequence is detectable when compared to the background. Further, it is desirable that the detectably labeled monoclonal antibody be rapidly cleared from the circulatory system in order to give the best target-to-background signal ratio.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

In some instances it may be advantageous to deliver and express a peptide sequence of the invention locally (e.g., within a particular tissue or cell type). For example, local expression of a peptide of the invention (e.g., a peptide having a sequence as set forth in SEQ ID Nos:2, 3, 4, 5, 6, 7, 8, or 9) in cartilage tissues, pancreatic tissue, skin tissue, or gut tissue of an animal. The nucleic sequence may be directly delivered to the tissue and cells, for example. Such delivery methods are known in the art and include electroporation, viral vectors and direct DNA uptake.

For example, a nucleic acid constructs of the present invention will comprise nucleic acid molecules in a form suitable for uptake into target cells within a host tissue. The nucleic acids may be in the form of bare DNA or RNA molecules, where the molecules may comprise one or more structural genes, one or more regulatory genes, antisense strands, strands capable of triplex formation, or the like. Commonly, the nucleic acid construct will include at least one structural gene under the transcriptional and translational control of a suitable regulatory region. More usually, nucleic acid constructs of the present invention will comprise nucleic acids incorporated in a delivery vehicle to improve transfection efficiency, wherein the delivery vehicle will be dispersed within larger particles comprising a dried hydrophilic excipient material.

One such delivery vehicle comprises viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. (1992) *CIRC. RES.* 71:1508–1517, the disclosure of which is incorporated herein by reference. A suitable adenovirus gene delivery is described in Rosenfeld et al. (1991) *Science* 252:431–434, the disclosure of which is incorporated herein by reference. Both retroviral and adenovirus delivery systems are described in Friedman (1989) *Science* 244:1275–1281, the disclosure of which is also incorporated herein by reference.

EXAMPLE 1

Peptide Identification

To identify the promiscuous pan-DR peptides a computer algorithm described in U.S. Pat. No. 6,037,135 (incorporated herein by reference in its entirety) that identifies motifs for binding of peptides to various MHC class II molecules was used. Sequences of both mycobacterial and human hsp60 were scanned, and based on the predicted binding of peptide sequences to three subtypes of HLADR, namely DR1, DR4 and DR7, peptides were designed (Table 1). The peptides were selected on the level of predicted binding to DR1, 4, and 7. The peptides of the present invention including those listed in Table 1 have been identified by in vitro tests for the ability to induce the proliferation of autoreactive T cells or to induce the secretion of cytokines (e.g., lymphokines) from these T cells or to induce other effector functions such as cytotoxicity.

An epitope identified by the computer algorithm was considered eligible when it was predicted to have sufficient affinity to HLA DR1, DR4 and DR7 (Pan-DR score=3). A 15-mer peptide was subsequently designed in such a fashion that at least two, but preferentially three, flanking amino acid residues were present at both sides of the predicted core epitope. Every peptide, containing a Pan DR binding epitope, was subsequently matched with its homologous (human or mycobacterial) counterpart. In this way, a total of 8 peptides were designed, 4 mycobacterial peptides (p1, p3, p5, p7) and 4 homologous human peptides (p2, p4, p6, p8). The peptides are shown in Table 1.

EXAMPLE 2

T-cell Proliferation

To test T cell proliferation a direct culture of Peripheral Blood Mononuclear Cells (PBMC) were contacted with the peptides of Table 1. Over 80 subjects with JIA were tested. The group consisted of a random selection of subjects with all subtypes of JIA, during different phases of disease activity and medical treatment. PBMC of subjects were tested in a standard proliferation assay. PBMC were isolated from heparinized blood using a Ficoll Isopaque density gradient. PBMC were cultured at a number of 200,000 cells per 200 microliter ($\mu$l) per well in 96 well round bottom plates in RPMI containing 15% AB serum. Cells were cultured for 6 days (120 hours) at 37° C. in 5% $CO_2$ with 100% relative humidity. During the last 16 hours of culture 1 $\mu$Ci (=37 kBq) tritiated thymidine was added to each well. Incorporated radioactivity was measured by liquid scintillation counting and expressed as counts per minute (cpm). The magnitude of the proliferative response was expressed as cpm and as stimulation index (SI): the mean cpm of cells cultured with antigen divided by the mean cpm of cells cultured with medium alone. A SI of 2 or higher can be considered positive response to an antigen. The results are shown in FIG. 1. A majority of subjects showed a positive T cell proliferative response to both human and mycobacterial whole hsp60, as could be expected from previous data. All hsp60 peptides induced peptide specific proliferative T cell responses in 40 to 60% of subjects of JIA.

Figure 2:
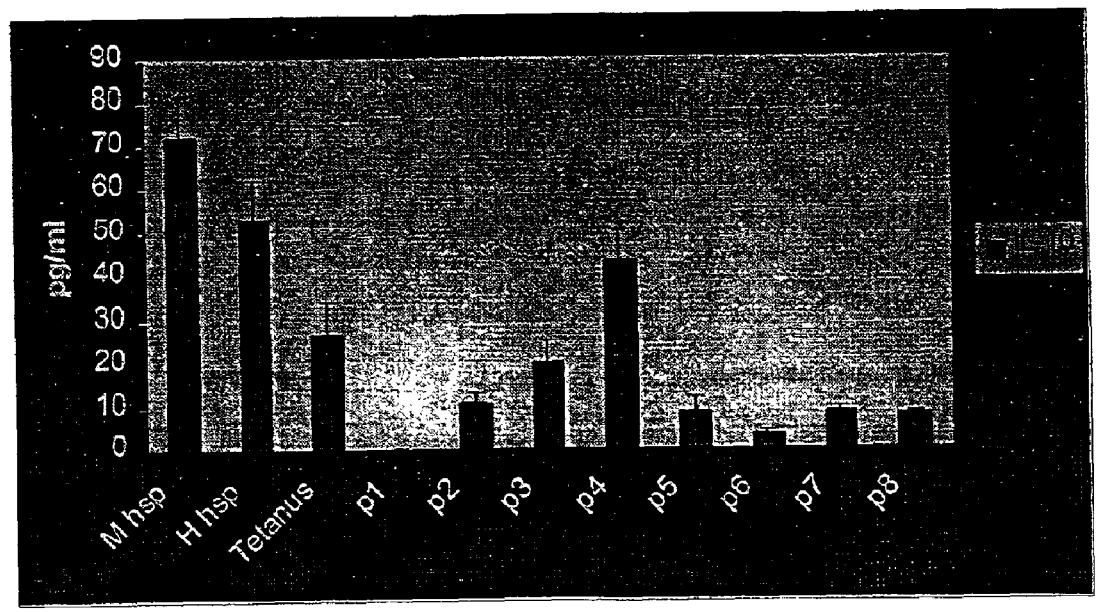
FIG. 2 shows antigen specific production of IL-10 after in vitro culture with the pan DR binding hsp60 peptides. ON the Y axis the production of IL-10 (in pg/ml) is shown in response to the different peptides. On the X-axis the different antigens used in this study: (from left to right) whole mycobacterial hsp60 (M hsp), whole human hsp60 (H hsp), tetanus, and the pan DR binding peptides p1–p8 (p1 (myc 254–268), p2 (hum 280–294), p3 (myc 216–230), p4 (hum 242–256), p5 (myc 210–224), p6 (hum 236–250), p7 (myc 503–517), and p8 (hum 535–546)).
Figure 3:
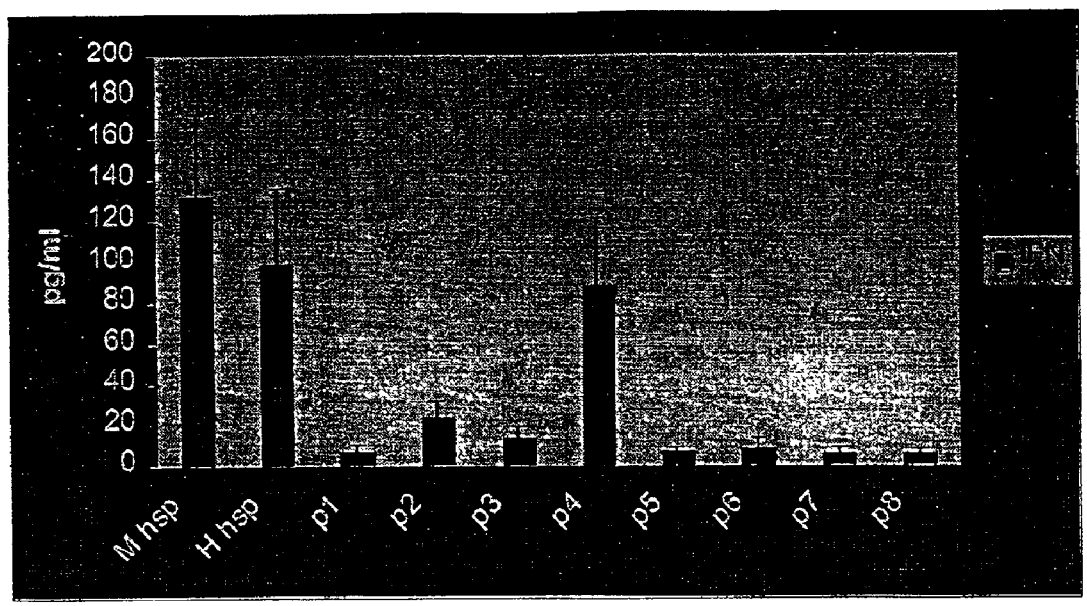
FIG. 3 shows the antigen specific production of Interferon-γ (IFN-γ) after in vitro culture with the pan DR binding hsp60 peptides. On the Y axis the production of Interferon-γ (in pg/ml) is shown in response to the different peptides. On the X-axis the different antigens used in this study: whole mycobacterial hsp60 (M hsp), whole human hsp60 (H hsp), tetanus, and the pan DR binding peptides (p1–p8). Negative control peptide mycobacterial hsp60 256–270 did not induce any cytokine production.
Figure 4:
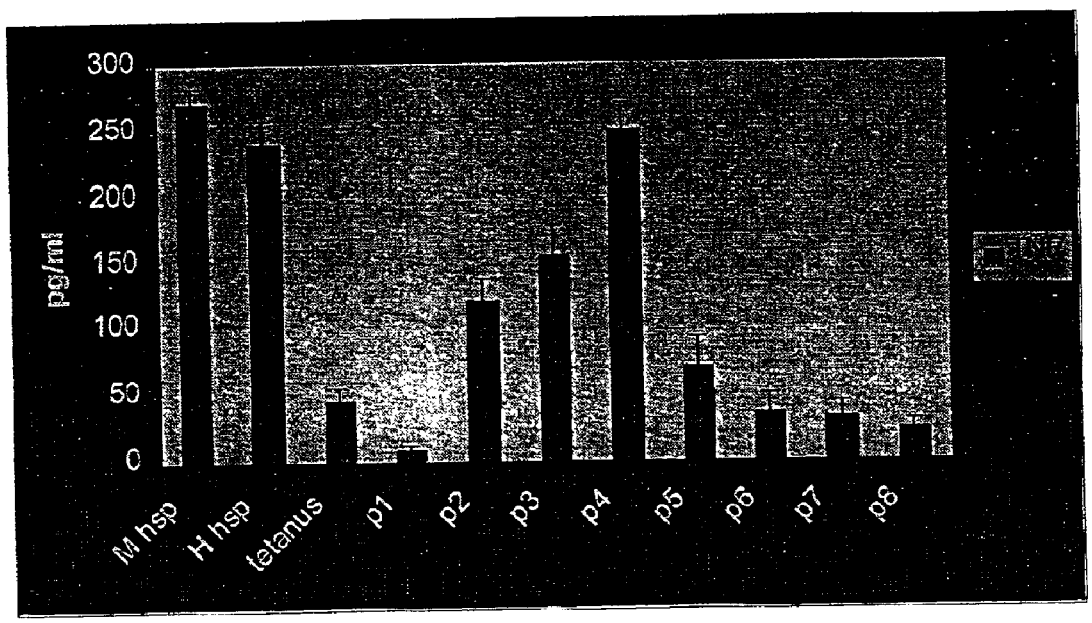
FIG. 4 shows the antigen specific production of TNF-α after in vitro culture with the Pan DR binding hsp60 peptides. On the Y-axis the production of TNF-α (in pg/ml) is shown in response to the different peptides. On the X-axis the different antigens used in this study: whole mycobacterial hsp60 (M hsp), whole human hsp60 (H hsp), tetanus, and the Pan DR binding peptides (p1–p8). The negative control peptide mycobacterial hsp60 256–270 did not induce any cytokine production.

In a smaller group of 18 subjects with JIA T cell proliferation was combined with measurement of antigen specific cytokine production. PBMC were cultured at 200,000 cells in 200 $\mu$l per well in a 96 well plate as described above. After 72 hours supernatants were removed and cytokine production was measured with a standard ELISA according to the manufacturer's protocol (B&D). The following cytokines were tested: IL-4, IL-10, IFN-$\gamma$, TGF-$\beta$, TNF-$\alpha$ and IL-1RA. FIG. 2–4 show the antigen specific cytokine production of IL-10, IFN-$\gamma$, and TNF-$\alpha$ after 72 hours of culture with the Pan DR binding peptides. Again, in a majority of subjects antigen specific cytokine production could be detected in PBMC cultured in vitro with the peptides. No antigen specific production of IL-4 could be detected, which is probably due to the sensitivity of the cytokine ELISA.

Figure 5:
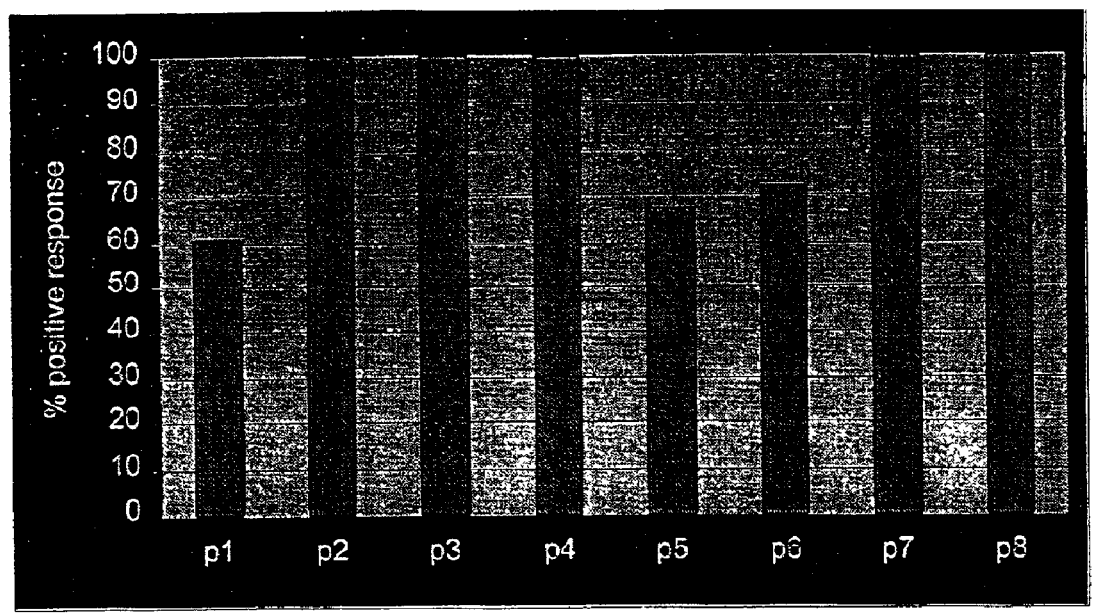
FIG. 5 shows the immunological recognition (defined as T-cell proliferation and/or production of cytokines) in response to hsp60 peptides of the invention in cells from 18 subjects with JIA.

Immunological recognition of an antigen can be defined as antigen specific T cell proliferation and/or antigen specific cytokine production after culture with the specific antigens. In addition, in a very high percentage of subjects (ranging from 60 to 100%) T cell recognition of these pan DR binding hsp60 peptides could be detected (FIG. 5). This percentage can be considered extremely high if one considers both the failures of previous studies to determine T cell epitopes in JIA and the heterogenic HLA background in subjects with JIA.

Figure 6:
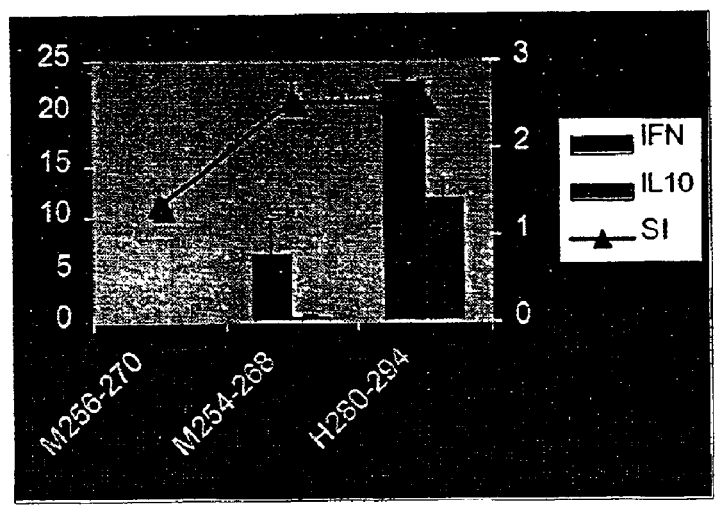
FIG. 6 shows a comparison of the immunological reactivity induced by peptide 256–270 compared to two peptides of the invention based on pan DR binding (p1, myc 254–268; and p2, hum 280–294). The right Y-axis depicts the stimulation index, and the left Y-axis depicts the production of cytokines in pg/ml.
Figure 7A:
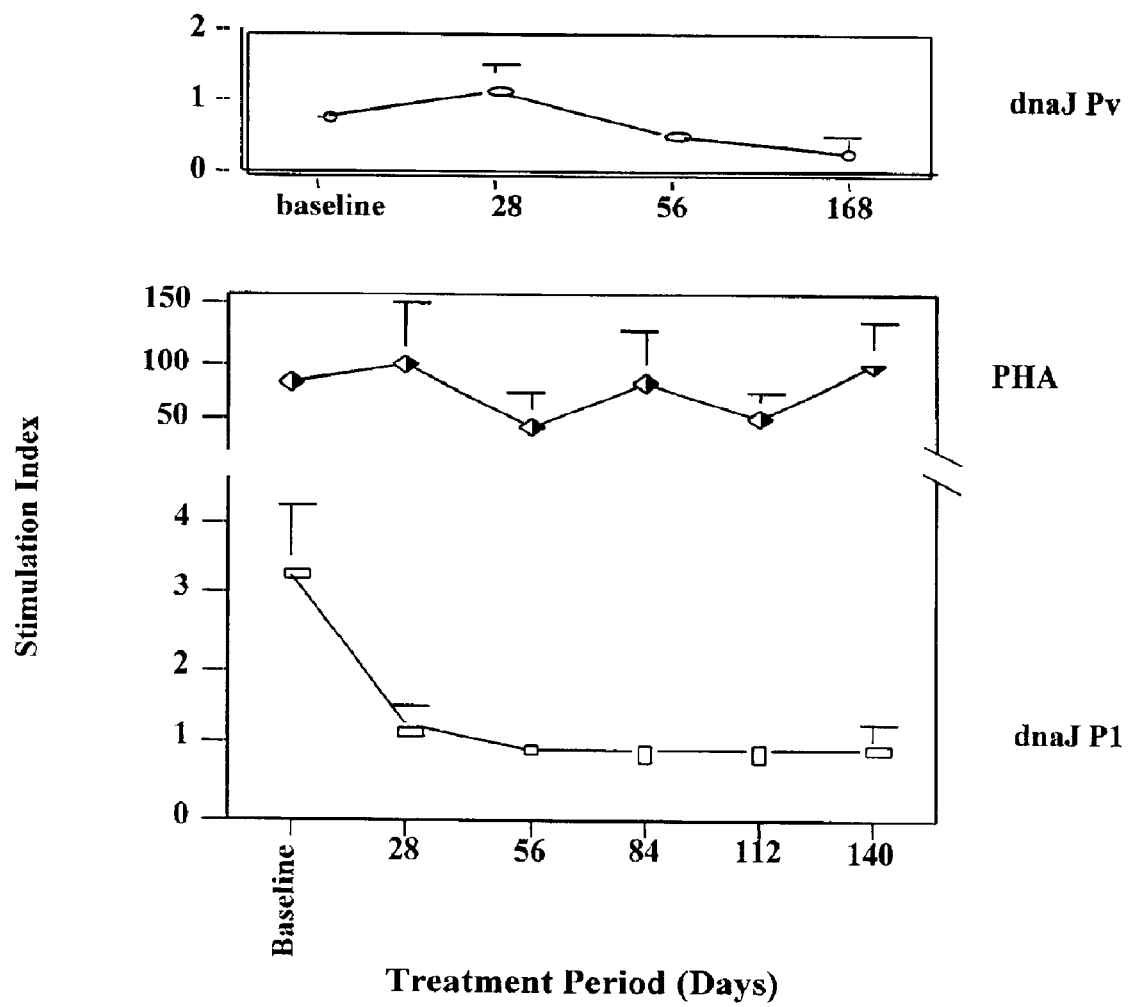
FIGS. 7A–E form a series of graphs showing treatment-induced modulation of T cell responses to dnaJP1.
Figure 7B:
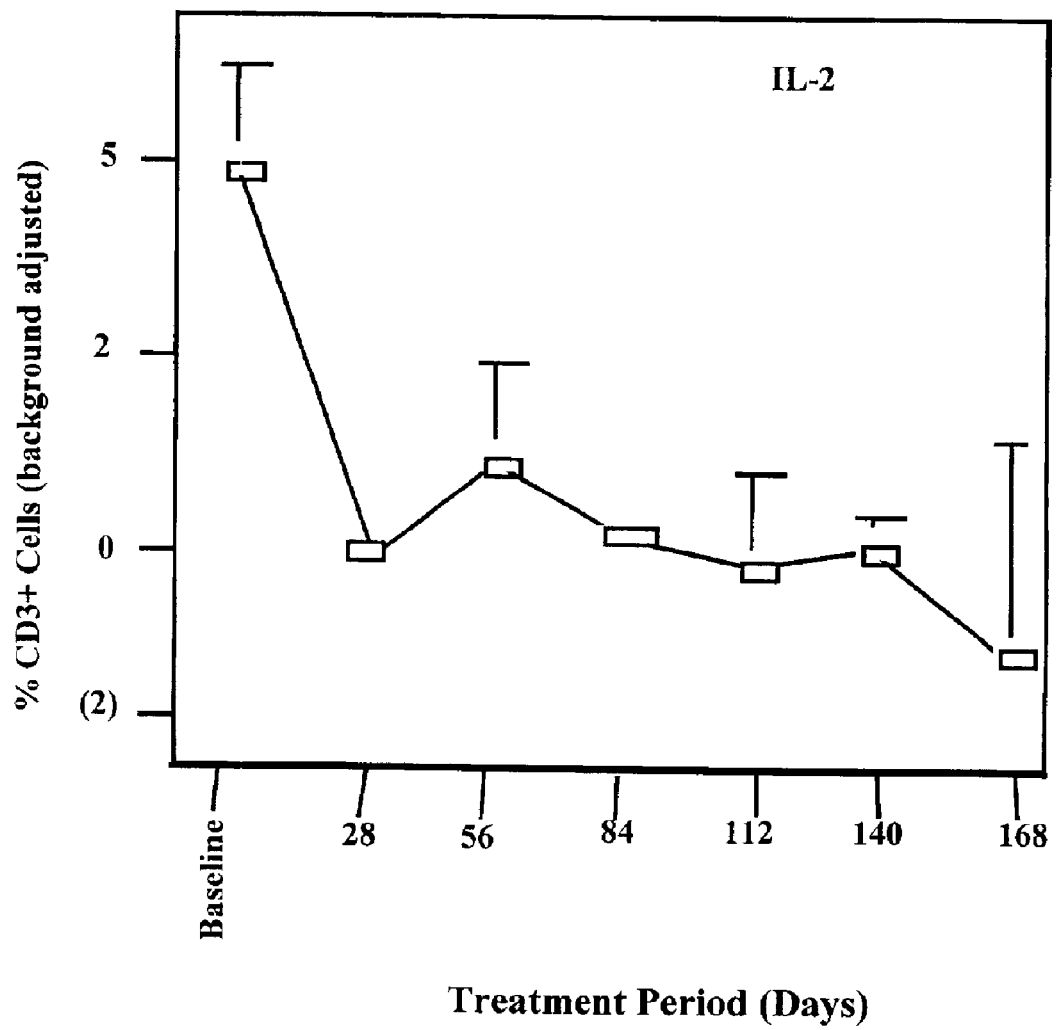
Figure 7C:
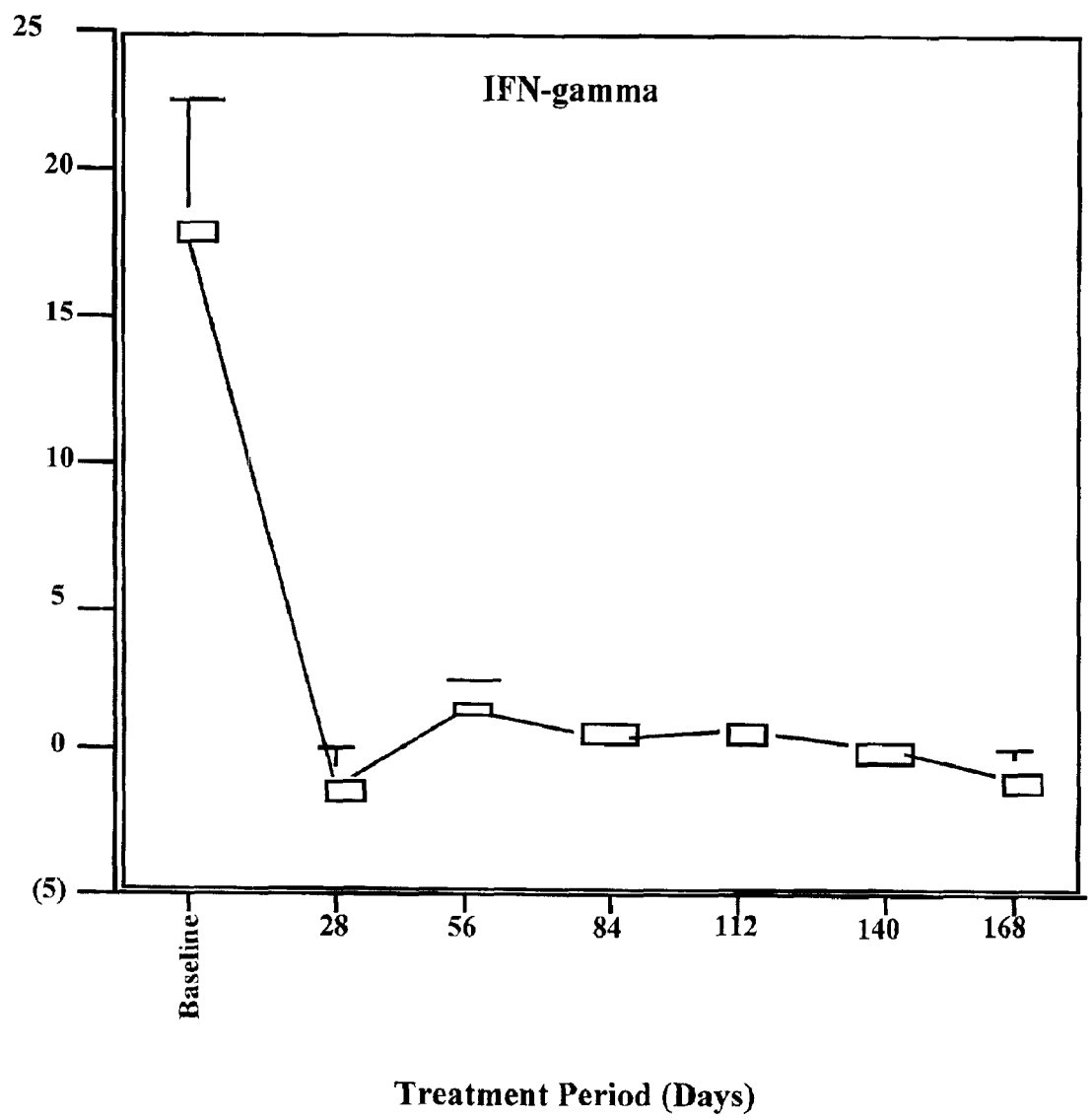
Figure 7D:
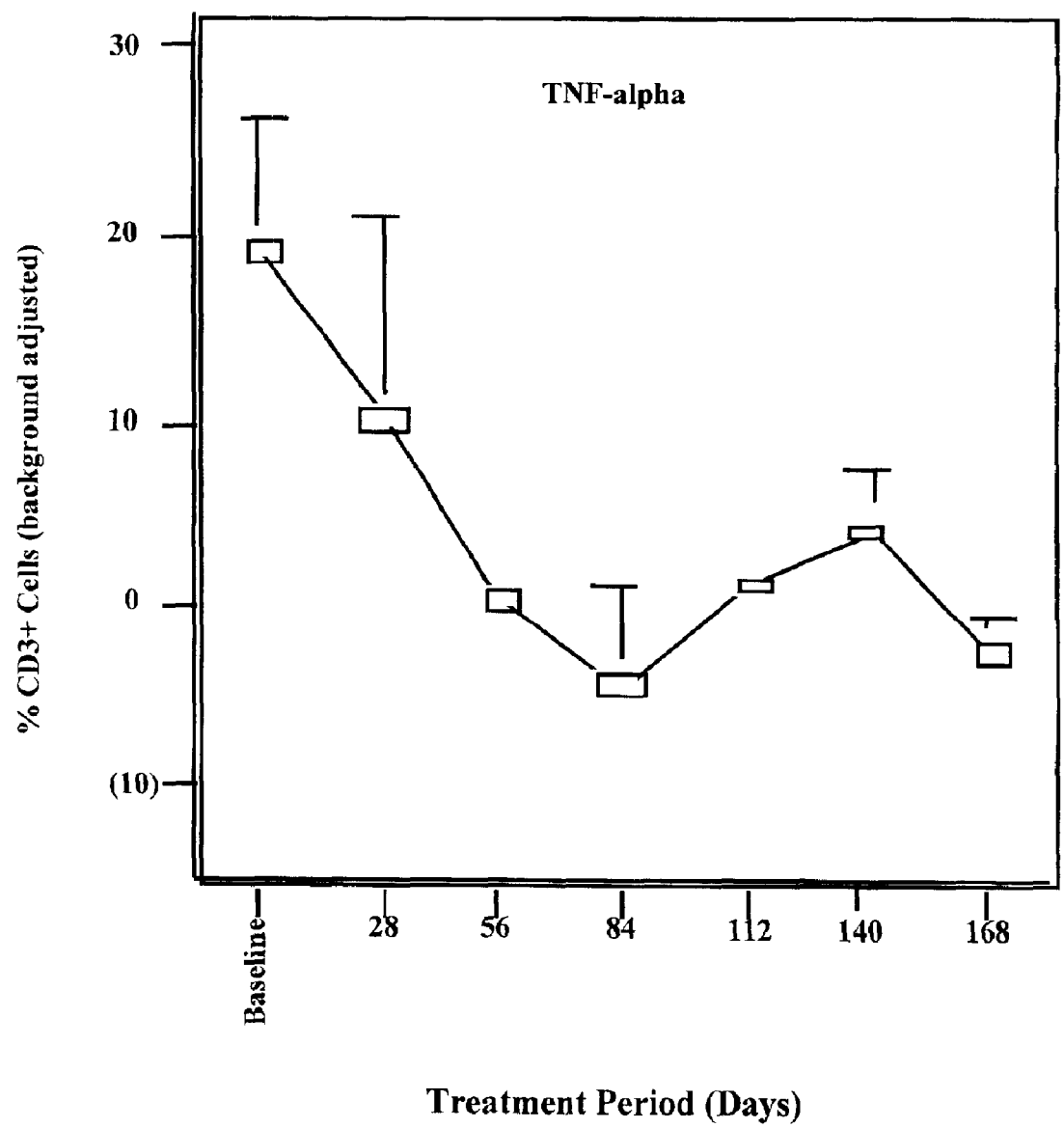
Figure 7E:
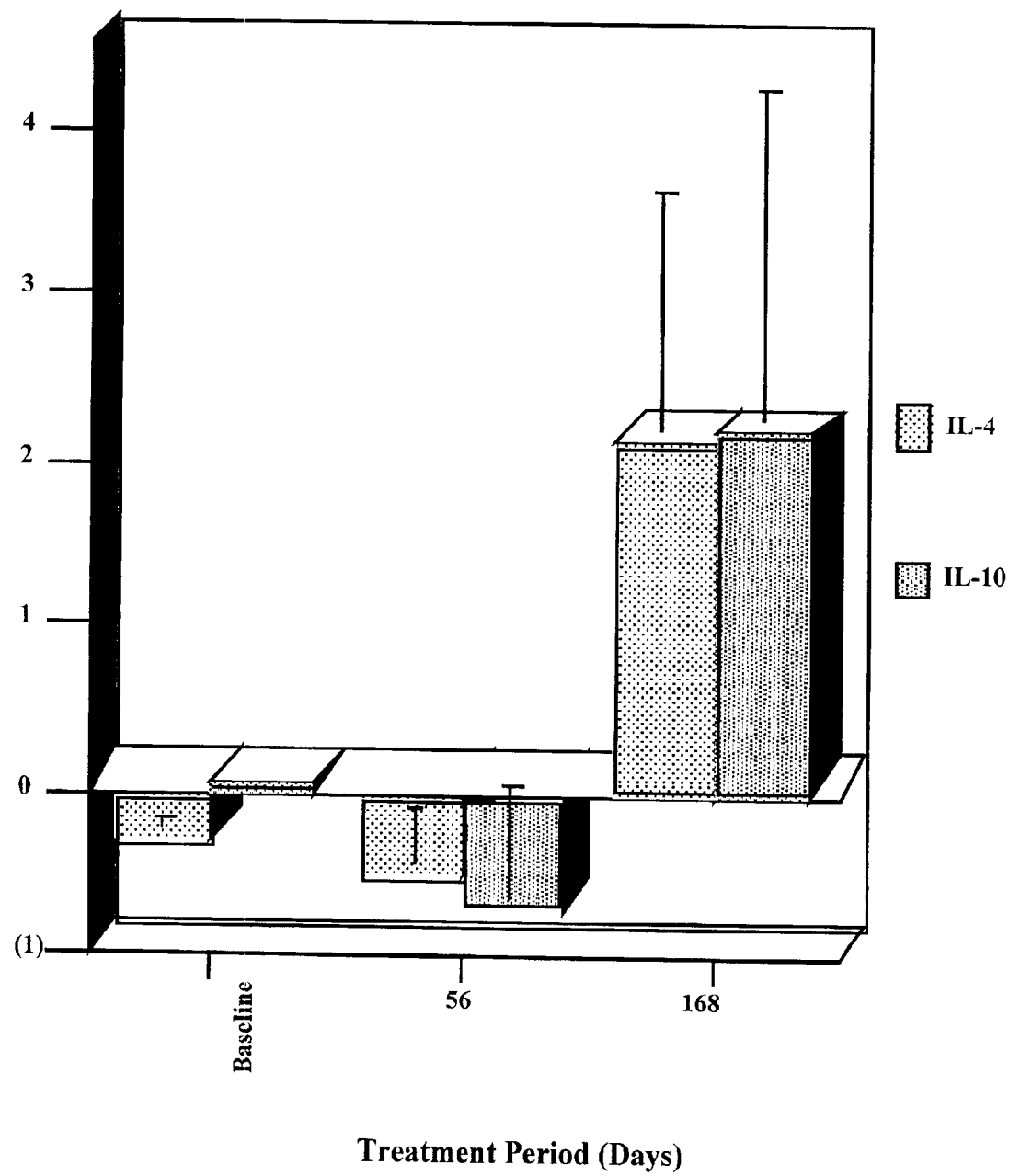
Figure 8A:
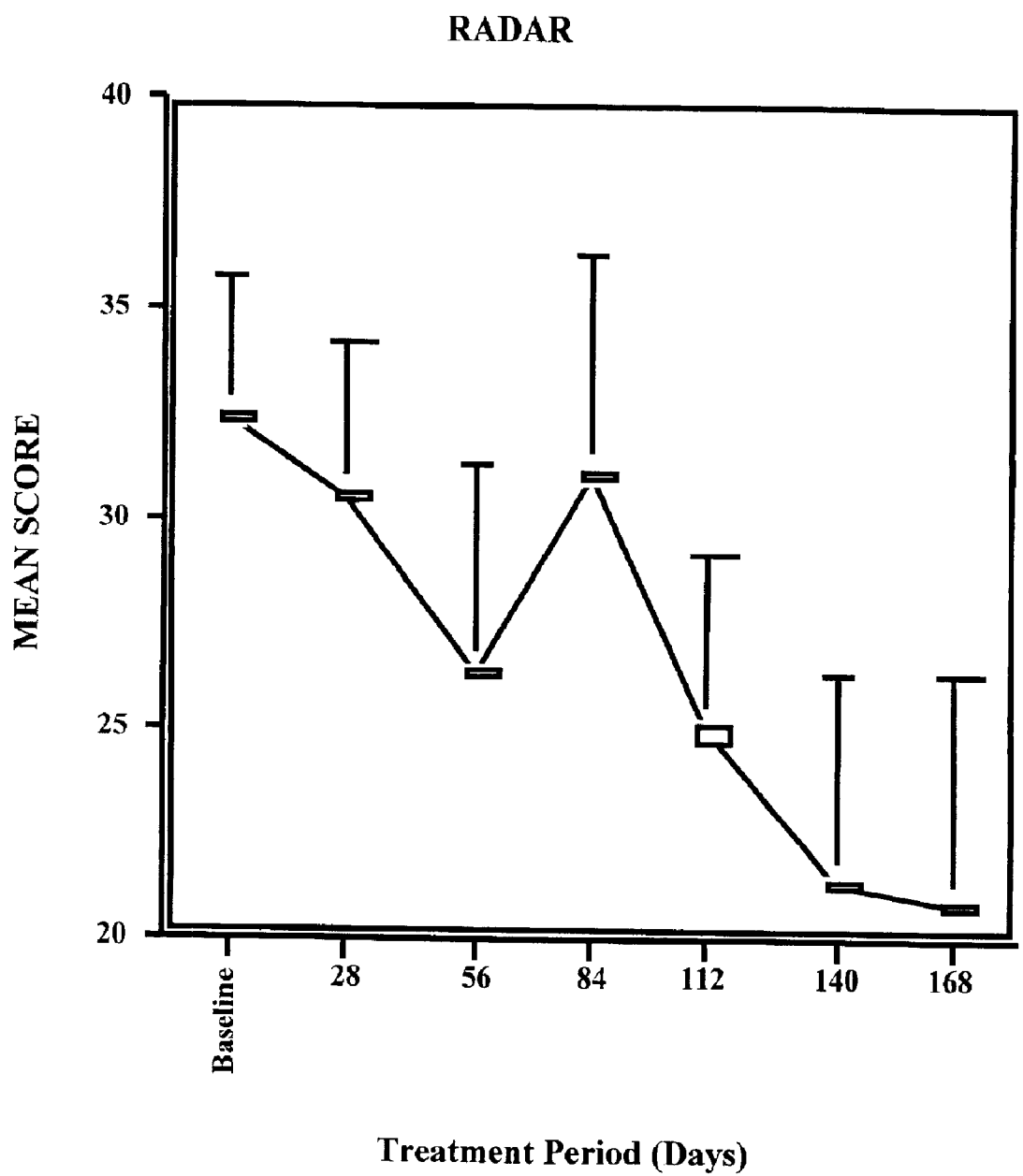
FIG. 8A is a graph showing the results of RADAR questionnaire for the subjects treated with dnaJ peptide. (*=p.<0.05)
Figure 8B:
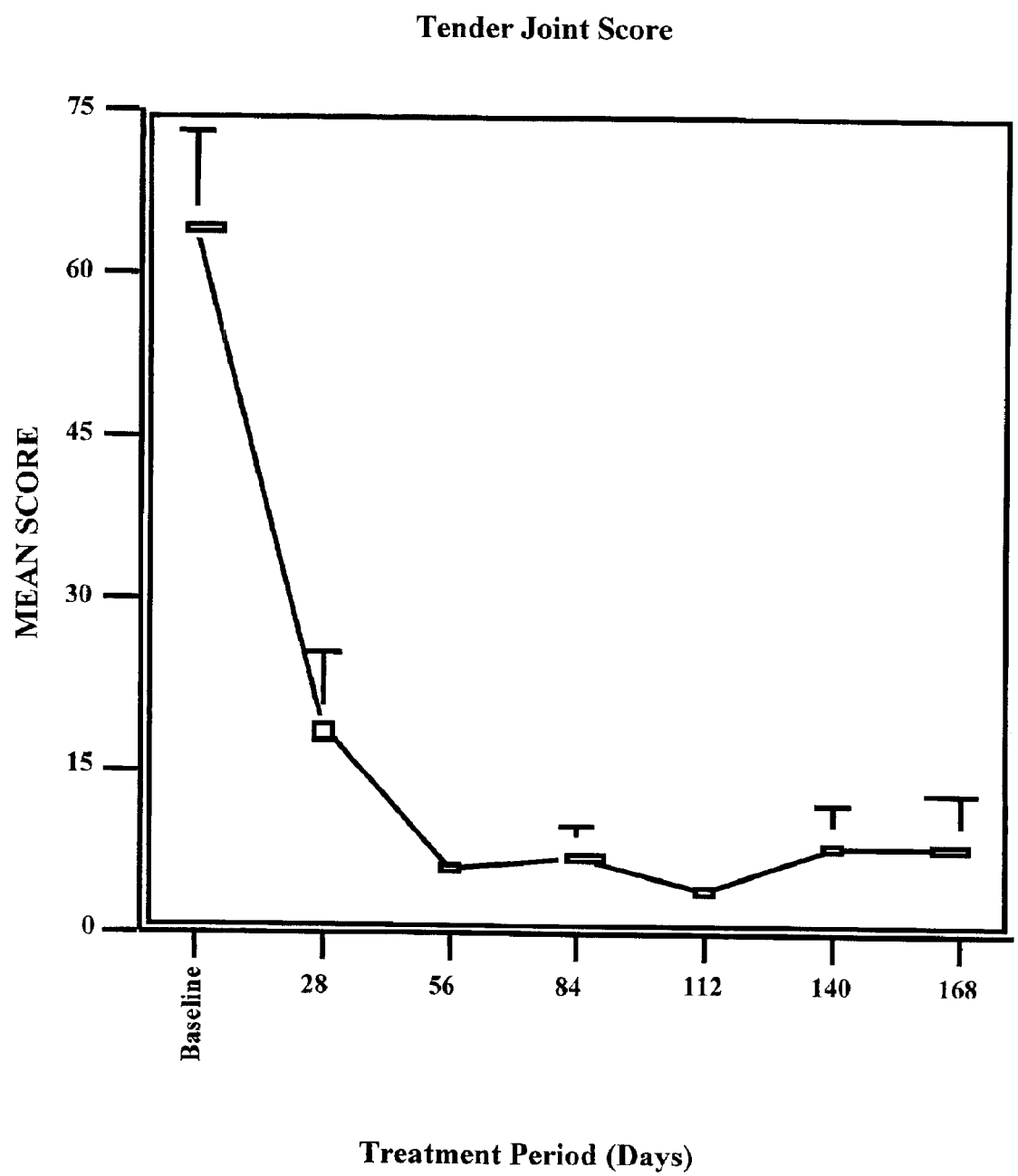
FIGS. 8B–E are graphs showing the tender and swollen joint counts (n=13) in subjects treated with dnaJ peptide.
Figure 8C:
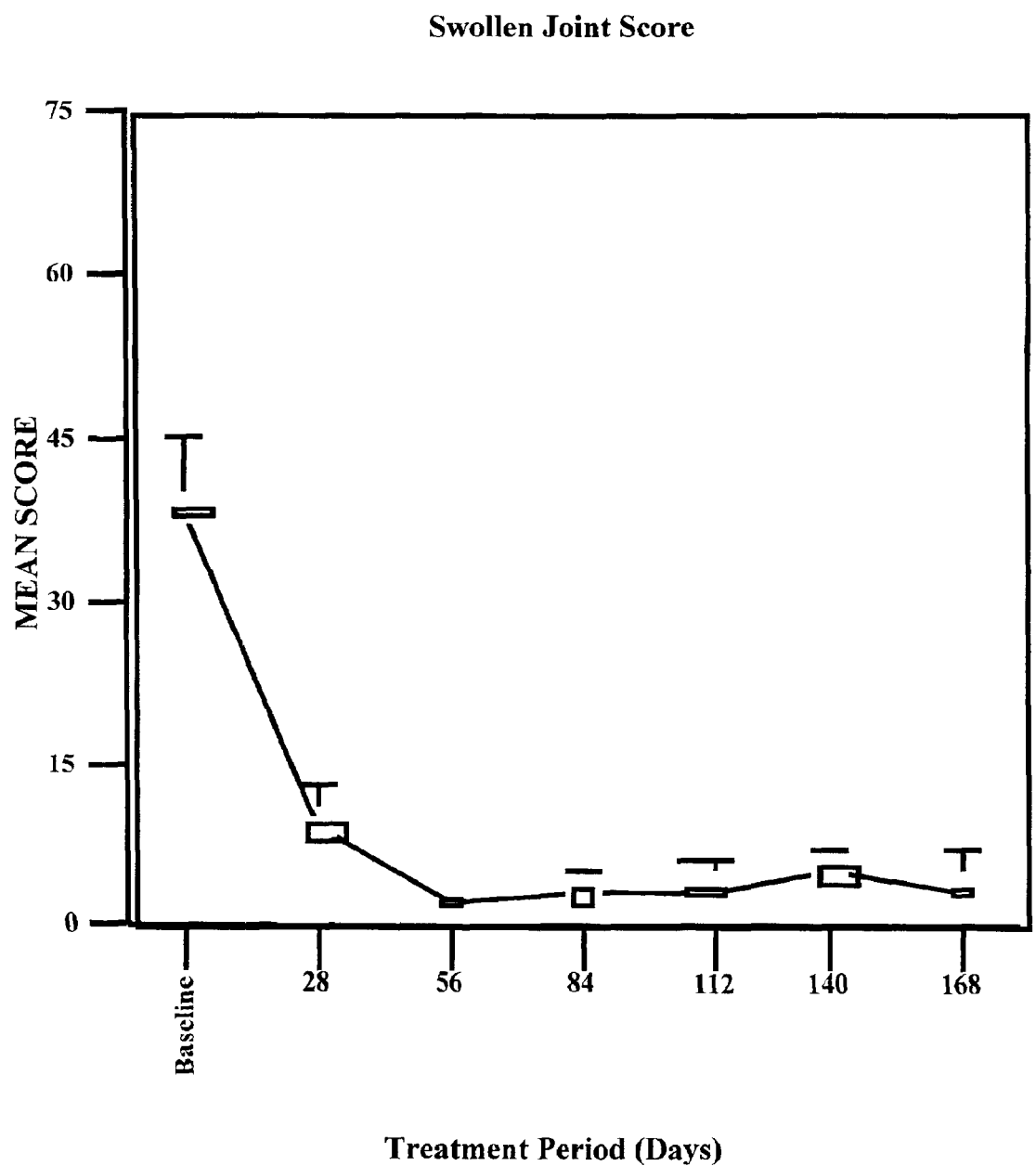
Figure 8D:
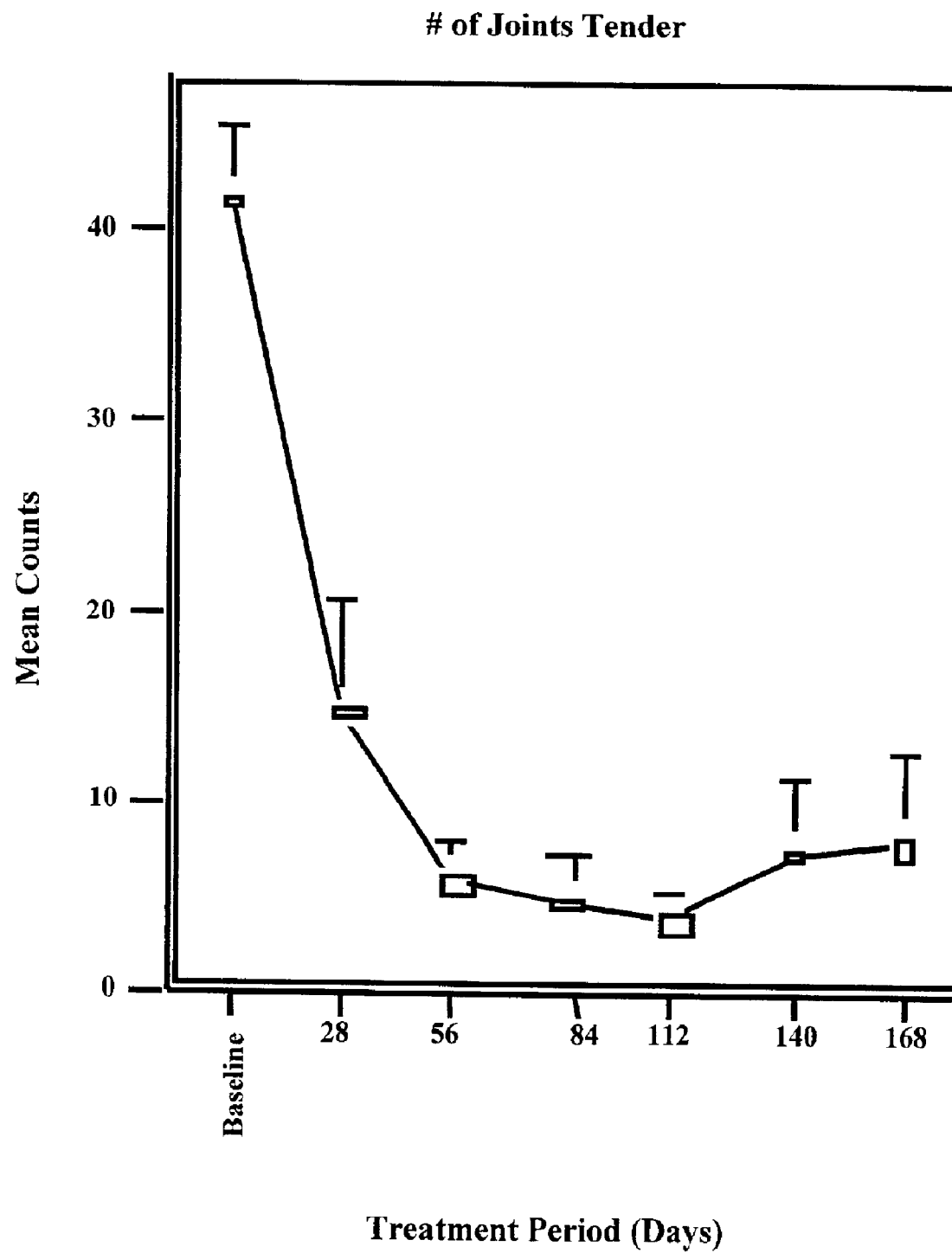
Figure 8E:
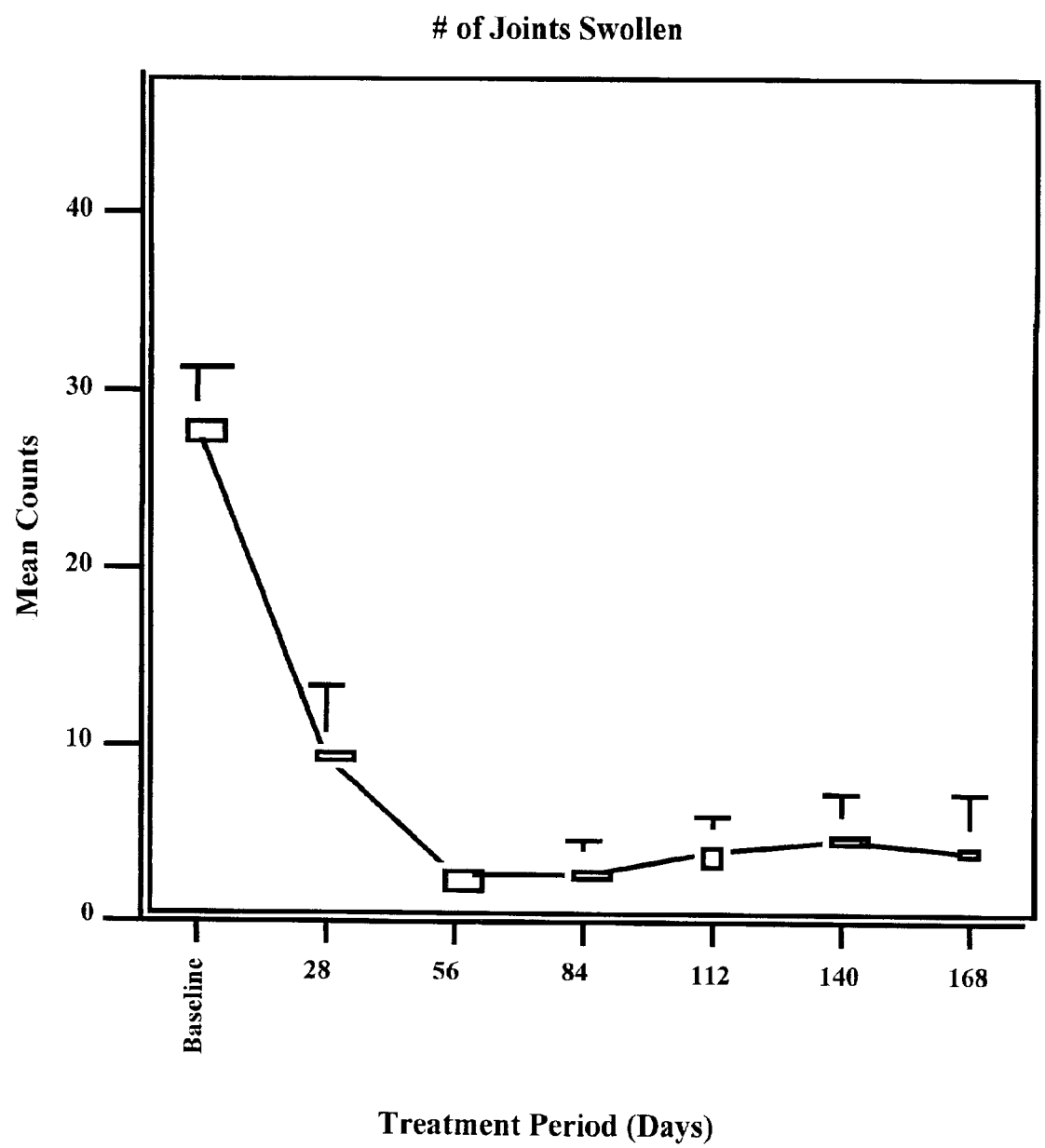

If one compares the thus identified peptides with peptides that previously have been identified through the rat model of arthritis, the superiority of the method used here becomes evident. In previous studies in the model of adjuvant arthritis it has been shown that mycobacterial hsp60 peptide containing amino acids 256–270 could induce protection in Adjuvant Arthritis. Following this finding a lot of effort has been put in attempting to identify the presence of 256–270 specific T cells in subjects with JIA. Based on the data provided by the computer algorithm we designed a new peptide that was compared to the 256–270 aa peptide. This new peptide, mycobacterial hsp60 254–268 (pI) did induce T cell responses as defined by T cell proliferation and cytokine production in a majority of JIA subjects; whereas the 256–270 peptide was not recognized in subjects with JIA. The data are shown in FIG. 6. Thus, using the predicted binding to DR1, DR4 and DR7 has provided a far more efficient way to identify T cell epitopes in subjects with JIA.

EXAMPLE 3

Identification of DNAJP1 as a Pro Inflammatory Epitope in Patients With RA

A peptide from the heat shock protein dnaJ was previously identified as a trigger of T cell proliferation and production of pro-inflammatory cytokines from peripheral blood and synovial fluid cells of RA patients. This peptide (dnaJP1:QKRAAYDQYGHAAFE) (SEQ ID NO:10), shares sequence homology with the "shared epitope", a five amino acid stretch in common among RA-associated HLA allels. This study is a Phase I Immune Tolerization study conducted to determine whether in RA interplay between HLA and dnaJ-derived peptides maintains and stimulates T cells, which participate in autoimmune inflammation. The trial (n of patients who completed=13) was designed in order to adhere to the American College of Rheumatology (ACR) 20 criteria for evaluation of efficacy.

Data from Phase I: The data shown in FIGS. 7A–E and 8A–E stem from a Phase I trial in which a total of 13 human RA patients were treated with three different doses of dnaJP1 qd po for 6 months. *Immunological Data*: in vitro T cell responses to dnaJP1 were monitored at monthly intervals by measuring T cell proliferation and cytokine production in patients treated by the invention peptide dnaJP1 and by controls. Controls comprised mitogens (PHA) and irrelevant peptides dnaJpV (DERAAYDQYGHAAFE) (SEQ ID NO:11), an altered ligand peptide that is not stimulatory in patients, and PADRE, a designer pan-DR binder peptide (KXVAAWTLKAA).(SEQ ID NO:12). The results of the T cell proliferative responses from PBMC of seven patients stimulated for 5 days with 10 µg/ml of dnaJP1 peptide are shown in FIGS. 7A–E (evaluations by FASC conducted at monthly intervals). Control experiments (not shown) for the FACS cytokine data analysis of FIGS. 7A–E included FACS measurement of the production of pro inflammatory intracellular cytokines IL-2, IFN-γ and TNF-α from PBMC of 4 patients from the clinical trial that were treated with PADRE. Controls also included FACS measurement of tolerogenic intracellular cytokines IL-4 and IL-10 produced by PBMC of 4 patients from the clinical trial treated with PADRE.

Given the cycling nature of RA, with remission and relapses, and the small number of patients studied, it was important to show that the immune changes found were treatment induced, and not dependent on a more general "state" of activation of a group of patients who, by chance, are cycling together.

FACS measurement was also obtained of tolerogenic intracellular cytokines IL-4 and IL-10 produced by PBMC from 4 untreated patients taken at three different time points and stimulated with dnaJP1. Results of the tolerogenic studies showed that the immune changes shown in FIGS. 7A–E are treatment-specific and treatment-induced.

FIGS. 8A–E show the results of (Rapid Assessment of Disease Activity in Rheumatology, RADAR) tests conducted by patient self-assessment in patients (n=13) stimulated with dnaJP1.

Even though every effort was made to preserve the integrity of the evaluation, it must be emphasized here that the nature of an open label trial like the Phase I herein described can provide only trends regarding treatment efficacy. 84.6% of the patients could be classified as responders according to ACR 20 criteria.

While the methods and compositions described above are typical of those that can be used to carry out certain aspects of the invention, other procedures known to those skilled in the art can also be used.

In addition, numerous modifications and variations of the present invention are possible in light of the above teachings and, therefore, within the scope of the appended claims, the invention may be practiced otherwise than as particularly described. It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other references mentioned herein are incorporated by reference in their entirety.

What is claimed is:

1. An isolated peptide having about 10 to 30 amino acid residues wherein at least 9 amino acid residues of the peptide consist of a sequence as set forth in SEQ ID NO: 18, SEQ ID NO: 20, or SEQ ID NO: 23.

2. An isolated peptide according to claim 1, wherein the peptide binds to HLADR1, DR4, and DR7.

3. An isolated peptide according to claim 1, wherein the amino acid sequence is selected from an amino acid sequence from human heat shock protein or a bacterial heat shock protein.

4. An isolated peptide according to claim 3, wherein the bacterial heat shock protein is a mycobacterial heat shock protein.

5. An isolated peptide having about 10 to 30 amino acid residues and having an amino acid sequence selected from the group consisting of SEQ ID NOs: 5, 7, 8, and 9.

6. An isolated peptide according to claim 5, wherein the stress protein is a heat shock protein.

7. An isolated peptide according to claim 6, wherein the heat shock protein is a bacterial heat shock protein.

8. An isolated peptide according to claim 6, wherein the heat shock protein is a mycobacterium species heat shock protein.

9. An isolated peptide according to claim 8, wherein the mycobacterium species heat shock protein is hsp65.

10. An isolated peptide according to claim 6, wherein the heat shock protein is a mammalian heat shock protein.

11. An isolated peptide according to claim 10, wherein the mammalian heat shock protein is a human heat shock protein.

12. An isolated peptide according to claim 11, wherein the human heat shock protein is human hsp60.

13. An isolated peptide according to claim 1, wherein the peptide is about 15 to 20 amino acids in length.

14. An isolated peptide according to claim 1, wherein the peptide has one or more D-amino acid residues.

15. An isolated peptide according to claim 1, wherein the peptide is covalently linked to an adjuvant.

16. An isolated peptide according to claim 15, wherein the adjuvant is keyhole limpet hemocyanin, bovine serum albumin, human serum albumin, or isologous IgG.

17. A pharmaceutical composition comprising a peptide according to claim 1 in a pharmaceutically acceptable carrier.

18. A composition comprising a pharmaceutically acceptable carrier and an isolated peptide according to claim 1.

19. A composition according to claim 18, wherein the peptide binds to at least one molecule selected from the group consisting of HLADR1, DR4, and DR7.

20. A composition according to claim 18, wherein the isolated peptide has an amino acid sequence selected from the group consisting of SEQ ID NOs: 5, 6, 7, 8, and 9.

21. A composition according to claim 18, further comprising a biological response modifier.

22. A composition according to claim 21, wherein the biological response modifier is selected from the group consisting of a cytokine, a chemokine, a hormone, a steroid, and an interleukin.

23. A composition according to claim 22, wherein the biological response modifier is an interferon.

24. A composition according to claim 21, wherein the biological response modifier is selected from the group consisting of IL-1($\alpha$ or $\beta$), IL-2, IL-3, IL-4, IL-5, IL-6, IL-7, IL-8, IL-9, IL-10, IL-11, IL-12, GM-CSF, M-CSF, G-CSF, LIF, LT, TGF-$\beta$, $\gamma$-LFN, TNF-1, BCGF, CD2, and ICAM.

25. An isolated peptide according to claim 1 that is chemically synthesized.

26. An isolated peptide according to claim 1 that is produced by recombinant expression.

27. An isolated peptide according to claim 1 or 5 or that is glycosylated.

28. A composition according to claim 18 that is a liquid formulation.

29. A composition according to claim 18 that is a solid formulation.

30. An isolated peptide wherein the amino acid sequence of the peptide consists of the amino acid sequence as set forth in SEQ ID NO: 6.

31. A composition comprising a pharmaceutically acceptable carrier and an isolated peptide, wherein the amino acid sequence of the peptide consists of the amino acid sequence as set forth in SEQ ID NO: 6.

32. An isolated peptide, wherein the amino acid sequence of the peptide consists of the amino acid sequence as set forth in SEQ ID) NO: 2.

33. A composition comprising a pharmaceutically acceptable carrier and an isolated peptide according to claim 32.

34. An isolated peptide, wherein the amino acid sequence of the peptide consists of the anino acid sequence as set forth in SEQ ID NO: 3.

35. A composition comprising a pharmaceutically acceptable carrier and an isolated peptide according to claim 34.

36. An isolated peptide, wherein the amino acid sequence of the peptide consists of the amino acid sequence as set forth in SEQ ID NO: 5.

37. A composition comprising a pharmaceutically acceptable carrier and an isolated peptide, wherein the amino acid sequence of the peptide consists of the amino acid sequence as set forth in SEQ ID NO: 5.

38. An isolated peptide, wherein the amino acid sequence of the peptide consists of the amino acid sequence as set forth in SEQ ID NO: 7.

39. A composition comprising a pharmaceutically acceptable carner and an isolated peptide, wherein the amino acid sequence of the peptide consists of the amino acid sequence as set forth in SEQ ID NO: 7.

40. An isolated peptide, wherein the amino acid sequence of the peptide consists of the amino acid sequence as set forth in SEQ ID NO: 8.

41. A composition comprising a pharmaceutically acceptable carrier and an isolated peptide, wherein the amino acid sequence of the peptide consists of the amino acid sequence as set forth in SEQ ID NO: 8.

42. An isolated peptide, wherein the amino acid sequence of the peptide consists of the amino acid sequence as set forth in SEQ ID NO: 9.

43. A composition comprising a pharmaceutically acceptable carrier and an isolated peptide, wherein the amino acid sequence of the peptide consists of the amino acid sequence as set forth in SEQ ID NO: 9.

* * * * *